United States Patent [19]

Cabasso et al.

[11] Patent Number: 4,728,429
[45] Date of Patent: Mar. 1, 1988

[54] MEMBRANE PERMEATION PROCESS FOR DEHYDRATION OF ORGANIC LIQUID MIXTURES USING SULFONATED ION-EXCHANGE POLYALKENE MEMBRANES

[76] Inventors: Israel Cabasso, 131 Buckingham Ave., Syracuse, N.Y. 13210; Emmanuel Korngold, P.O. Box 1025, Beer-Sheva 84110, Israel

[21] Appl. No.: 749,503

[22] Filed: Jun. 27, 1985

[51] Int. Cl.$^4$ .............................................. B01D 13/00
[52] U.S. Cl. ..................... 210/638; 210/640; 210/500.36
[58] Field of Search ............ 210/640, 500.2, 34.1, 210/638, 500.36; 521/27

[56] References Cited

U.S. PATENT DOCUMENTS

| | | | |
|---|---|---|---|
| 2,416,061 | 2/1947 | McAlevy et al. | 260/27 |
| 2,586,363 | 2/1952 | McAlevy | 260/79.3 |
| 3,043,891 | 7/1962 | Stuckey | 210/640 X |
| 3,723,306 | 3/1973 | Bridgeford | 210/500.36 X |
| 3,950,247 | 4/1976 | Chiang et al. | 210/640 X |
| 4,073,754 | 2/1978 | Cabasso et al. | 260/17 R |
| 4,075,093 | 2/1978 | Walch et al. | 210/23 H |
| 4,115,465 | 9/1978 | Elfert et al. | 260/674 R |

FOREIGN PATENT DOCUMENTS 1412456 11/1925 United Kingdom .......... 210/500.36
 981562  1/1965 United Kingdom .......... 210/500.36

OTHER PUBLICATIONS

M. H. V. Mulder, et al., 16 *J. Membr. Sci.*, 269-284, (1983).
Israel Cabasso, 22(2), *Ind. Eng. Chem. Prod. Res. Dev.*, 313-319, (1983).
Hwang et al., *Membranes in Separations*, 99-116, (John Wiley & Sons, 1975).
K. Jobst et al., 13(10), *Plaste und Kautschuk*, 579-582, 1966.
*Chem. Abstr.*, vol. 75, 1971, No. 52662k, p. 234.
*Chem. Abstr.*, vol. 76, 1972, No. 117314r, p. 310, No. 131247c, p. 296.

Primary Examiner—Frank Spear
Attorney, Agent, or Firm—Morgan & Finnegan

[57] ABSTRACT

A membrane permeation process for dehydrating a mixture of organic liquids, such as alcohols or close boiling, heat sensitive mixtures. The process comprises causing a component of the mixture to selectively sorb into one side of sulfonated ion-exchange polyalkene (e.g., polyethylene) membranes and selectively diffuse or flow therethrough, and then desorbing the component into a gas or liquid phase on the other side of the membranes.

30 Claims, 11 Drawing Figures

FIG. I

•—•  SULFONATED POLYETHYLENE MEMBRANE
WITH Cs⁺ COUNTER-ION

ISOPROCANOL —+——+— ETHANOL —o——o—
METHANOL —□——□—

WATER FLUX —+—+—47.0% $H_2O$ —o—o—22.6% $H_2O$

ETHANOL FLUX —□—□—47.0% $H_2O$

MEMBRANE PERMEATION PROCESS FOR DEHYDRATION OF ORGANIC LIQUID MIXTURES USING SULFONATED ION-EXCHANGE POLYALKENE MEMBRANES

BACKGROUND OF THE INVENTION

1. Field of the Invention

The present invention relates to a process for separating organic liquid mixtures, such as alcohols from mixtures with water, using sulfonated ion exchange polyalkylene (polyalkene) membranes.

2. Description of Prior Art

Azeotropic mixtures or close boiling mixtures are separated at present on a large scale by multistage distillation (rectification) or, sometimes, by a combined process such as extractive distillation. These separation processes are characterized by: high energy demands, relatively large capital plant investments, a variety of maintenance problems, and severe environmental problems that contribute to the energy demands. For example, high temperature multistage distillation increases thermal loads on the cooling system of a chemical plant and generally contributes to water and air pollution. Government regulations, which are designed to mitigate these problems, often constitute an additional energy burden on the separation process.

The need to use energy efficiently, combined with the sharp rise in the cost of petroleum products, have focused attention on by products of the chemical and petroleum industries. Most of these by products consist of mixtures of liquid organic compounds, whose separation is often complicated and costly. Therefore, some of the by products have been considered, until recently, as expendable and disposable, or were burned to provide very expensive energy. The development of a low-cost technique of separating such mixtures would clearly be of great benefit.

Separation processes which involve the use of porous and/or semi-permeable membranes for separating compounds from each other have been used for solving many problems. For example, membrane separation processes have been applied in biotechnology. Conventional separation techniques such as distillation, adsorption, liquid-liquid extraction and crystallization are often insufficient and uneconomical. Application of membrane technology can save in process costs because energy consumption is low, raw materials and nutrients can be recovered and reused, fermentation processes can be carried out continuously, and disposal problems can be reduced or eliminated. See, Lee et al., ("Membrane Separations in Alcohol Production", 369 *Ann N.Y Acad Sci.* 367 (1981), who propose to achieve cost savings by using membrane processes, such as ultrafiltration, reverse osmosis and electrodialysis, in combination with distillation.

Membrane permeation by the pervaporation process involves selective sorption of a liquid mixture into a membrane, diffusion through the membrane, and desorption into a vapor phase on the permeate side of the membrane. Because of the interesting potential applications of pervaporation techniques, for example, to the separation of organic liquid mixtures, attempts have been made to discover commercially acceptable membranes.

Binning et al., 37 *Pet. Refiner.* 214 (1958); and Binning et al., 3(1) *E.C. Am. Chem. Soc. Div. Pet. Chem. Prepr.* 131 (1958) describe separation of organic liquid mixtures by synthetic membranes, and in particular, the economics of drying 2-propanol via a selective synthetic membrane, claiming that the membrane separation process was more feasible than a conventional azeotropic distillation with hexane. Elaborate analyses of such processes are described in Choo, 6 *Pet. Chem.* 73 (1962). Numerous studies dealing with separating organic liquids via pervaporation processes have been reported. Nevertheless, this technology has not kept pace with other membrane separation processes such as reverse osmosis, electrodialysis and hemodialysis, which have been commercialized. The reasons, among others, have been the poor separations obtained from commercial films, e.g., polyethylene (See Huang et al. 12 *J. Appl. Polym. Sci.* 2615 (1968)), that served as membrane components, and the lack of proven feasibility of the conventional pervaporation process.

Mulder et al. "Ethanol Water Separation by Pervaporation", 16 *J. Membr. Sci.* 269–284 (1983) summarize selectivities and permeation rates when dense homogeneous membrane materials were used to separate ethanol-water mixtures reported in the literature. The membrane materials include cellulose acetate, cellulose, polytetrafluoroethylene (PTFE)-polyvinylpropylene, cellophane, PTFE-polysulfone, polyethylene, polyethylenetetrafluoride, and polyvinylalcohol. The reported selectivities and permeation rates for these materials were very low with selectivities from less than 0.0006 to 11 and permeation rates from less than 0.01 to 9.46 (cm/hr). Mulder et al. also report selectivities and permeation rates of other homogeneous membrane materials they tested at thickness from 10 to 30 micrometers, including cellulose acetate, cellulose triacetate, cellulose tripropionate, cellulose acetate butyrate, polyacrylonitrile (PAN), polyvinylidenefluoride, polysulfone (PS) and polydimethylsiloxane. The reported selectivities and permeation rates for these other materials except for PAN and PS also was very low with selectivities from 0.3 to 4.1 and permeation rates from 0.017 to 0.113 (cm/hr). The selectivities reported for PAN (70) and PS (332) appear high, but combined with the low permeation rates (flux through the membrane) reported for PAN (0.0015 cm/hr) and PS (0.0004 cm/hr) render such membrane materials of little or no practical utility.

Pervaporation membranes for selective separation of water from aqueous starting mixtures containing organic and inorganic dissolved constituents are mentioned in *Chem. Abstr.*, Vol. 76, 1972, No. 117314r, page 310 (nitrogen-free membrane containing at least one homo-, or copolymer of at least one polyester, polyketone, polysulfone and may contain maleic anhydride, maleic acid, vinylsulfonate, vinylbenzoic acid); and in *Chem. Abstr.*, Vol. 72, 1972, No. 131247c, page 296 (membrane made of mixed polymers of acrylonitrile and acrylic acid).

The use of three types of dense isotropic membrane materials: (1) alloys of polyphosphonyl esters and cellulose acetate; (2) a highly cross-linked quarternary derivative of polyphenylene oxide; and (3) an ion exchange membrane consisting of sulfonic acid groups attached to a fluorohydrocarbon matrix (copolymers of polysulfonyl fluoride vinyl ether and polytetrafluoroethylene (PTFE)) (available as Nafion 125 TM from E. I. DuPont DeNemours & Co., Wilmington, Del.), as pervaporation membranes is reported in Cabasso, 22 *Ind. Eng. Chem. Prod. Res. Dev.* 313 (1983). The membranes were used for the separation of four liquid mixtures: (1) methanol/benzene 26.9/73.1 (percent composition in azeotrope); (2) benzene/cyclohexane, 55/45 (percent composition in azeotrope); (3) cyclohexane/cyclohexane; and (4) styrene/ethylbenzene, composed of a copolymer of polysulfonylfluoride vinyl ether and polytetrafluoroethylene blocks.

Cabasso reports, for example, for the separation of methanol-hexane mixtures, separation factors higher than 50 accompanied by high permeation were attained by employing an ion-exchange Nafion 811 TM membrane U.S. Pat. No. 2,953,502 describes the separation of benzene from an azeotropic mixture of benzene and methanol by means of a non porous polyethylene membrane. U.S. Pat. No. 4,073,754 to Cabasso et al. describes the use of pervaporation membranes for separation of aromatic hydrocarbons such as benzene, cyclohexane, ethanol, from other organic solvents, e.g., aliphatic hydrocarbons such as cyclohexane, decalin, heptane. The membrane materials employed consisted of a polymer alloy of poly (vinylidenechloride-benzyldiethyl phosphone) copolymer and acetyl cellulose; a phosphonylated poly(phenylene)oxide derivative and acetyl cellulose; and poly(2-methyl-6-methylenedimethylphosphonate-3-bromo-1, 4-phenylene) oxide.

SUMMARY OF THE INVENTION

1. Objects of the Invention

It is an object of this invention to provide a simple and effective process for selectively separating a mixture of an organic liquid and water.

Another object of the present invention is to provide a membrane permeation technique employing permselective polymer membranes for efficiently separating organic liquid mixtures such as a water/alcohol mixture.

An object of this invention is to provide highly effective permselective membranes which are useful in separating organic liquid mixtures such as water/alcohol mixtures.

It also is an object of this invention to provide a membrane permeation technique which can be used to dehydrate alcohols and separate organic liquid, mixtures and their related aqueous azeotropes.

Still another object of the present invention is to provide membrane permeation techniques which can be used to achieve almost complete separation and dehydration of water/alcohol mixtures in one stage.

An object of this invention is to provide a durable permselective polymer membrane which can be tailored to yield desired permselectivities.

Additional objects and advantages of the invention will be set forth in part in the description, or may be realized by practice of the invention, the objects and advantages being realized and attained by means of the methods, processes, instrumentalities and combinations particularly printed out in the appended claims.

DESCRIPTION OF THE DRAWINGS

Referring now to the drawings.

2. Brief Description of the Invention

Figure 1:
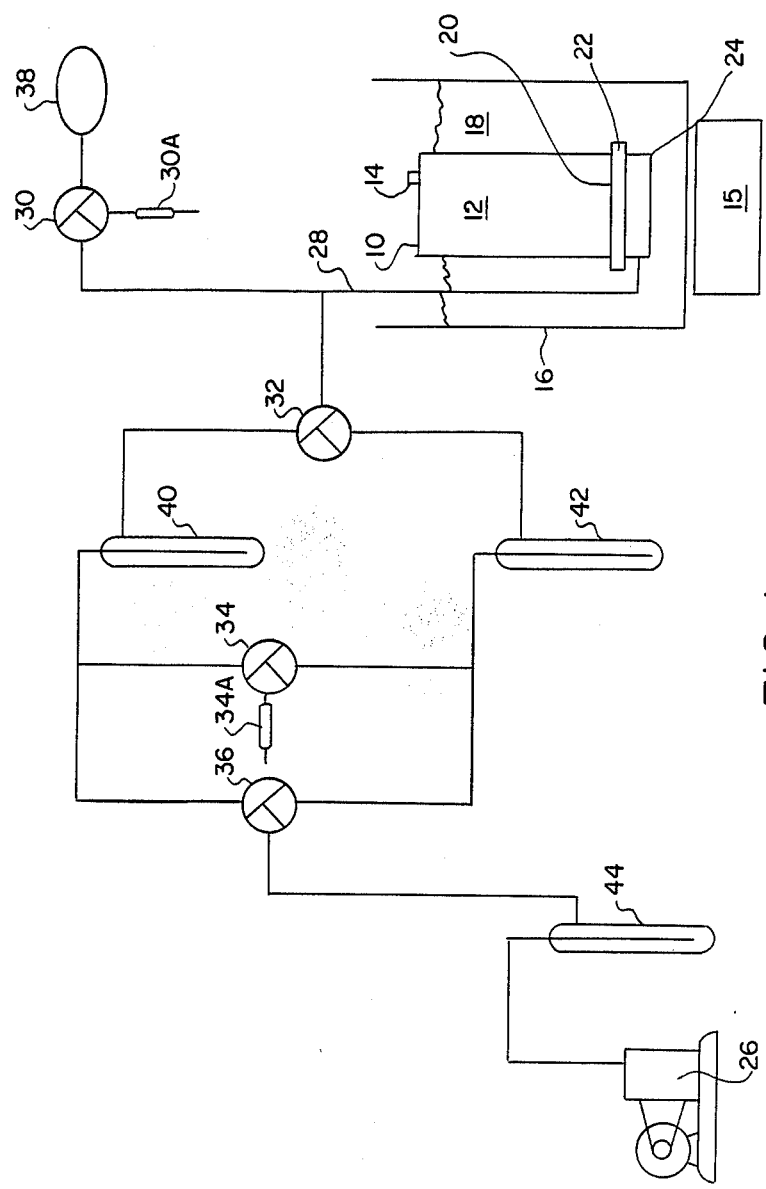
FIG. 1 is a schematic view of a pervaporation process employing a stirred high pressure static cell containing a flat sheet membrane according to this invention.

Briefly, this invention relates to a process for dehydrating organic liquids, such as an alcohol/water mixture, or close boiling heat sensitive mixtures, which process comprises:

causing a component of the mixture to selectively sorb into one side of sulfonated ion-exchange polyalkene membranes, referred to herein as the up stream side, and selectively diffuse or flow through the membranes; and desorbing the component, preferably into a vapor phase, on the other side of the membranes, referred to herein as the downstream side.

When the component which permeates through the membranes emerges as low partial vapor pressure gas at the downstream side of the membranes, the component may be condensed into a liquid or solid state employing refrigeration.

The process of dehydrating organic liquid mixtures according to applicants' invention may be accomplished by the membrane separation techniques of pervaporation; osmotic distillation; osmotic distillation with a selective acceptor liquid; osmotic phase separation; or by stripping with gas. According to such techniques, in general, a feed mixture is brought into contact with a thin amorphous polymer film, a permeant comprised of a component of the feed mixture or the feed mixture enriched with the component permeates the film (membrane) by a diffusion mechanism along a concentration gradient, the permeate is stripped from the membrane "downstream" side (the side opposite to the feed mixture). Each technique or process prevails by maintaining a low chemical potential for the permeate at the downstream side. The practical methods that are employed in such processes have a large impact on the separation efficiency (e.g., separation factor, permeation rate, energy consumption).

In the pervaporation process, the downstream side is maintained as a gas phase at a low permeate vapor pressure, for example, a reduced pressure of down to 100 Pa. The permeating component evolves at the downstream side in a gaseous state, and is condensed and collected, as a liquid or solid.

By creating a low chemical potential for the permeate at the downstream side, mass transfer of the permeating component is spontaneous. Efficiency of the process depends on the permeation rate and the capability to approach the minimum energy consumption in the transfer from the downstream side to the condensation and collection means. The major energy requirement for the process is in this transfer of permeate, i.e., the conversion of the permeant into a pure (bulk) liquid phase. In the pervaporation process, the concentration gradient is established by a reduced vapor pressure (vacuum) at the downstream side. The permeating component evolves from the membrane(s) in a gaseous stage, and the transfer from the downstream side to the collection means is a condensation process.

In the osmotic distillation process, the permeate is stripped from the membrane's downstream surface by circulating an acceptor (purge) liquid at the membrane interface (downstream side). The transition from the downstream side to the collection means then requires the removal of the permeate from the purge liquid in a simple distillation or by evaporation.

In the osmotic distillation process with a selective acceptor liquid, separation is improved by circulating, at the membrane interface (the downstream side), a non-permeable acceptor liquid which is compatible with only one of the organic components in the mixture to be separated.

In the osmotic phase separation process, the permeate is stripped from the membrane's downstream surface by circulating, at the membrane interface (the downstream side), a non permeable accepto fluid which is compatible with the permeate at a certain temperature region, $T_2$. The solution of acceptor fluid and permeate is decomposed at a different temperature, $T_1$, into two phases, one of which is rich in permeate.

In the process involving stripping with a gas, a stream of gas, e.g., air, is used as the acceptor fluid at the membrane's interface (the downstream side) to strip permeate from the membrane's downstream surface.

Applicants' process is particularly suited for separating/dehydrating organic liquid mixtures. Suitable organic compounds have a miscibility of at least about 5% in water. A preferred permeate is water which often can be disposed without condensation. Thus renders the process highly feasible due to its low cost and its low energy demand.

Suitable organic compounds are believed to include alcohols, ethers, carboxylic acids, aldehydes, ketones, acid chlorides, anhydrides, amides, esters, sulfonic acids, amines, phenols, aryl halides, glycols, dicarboxylic acids, keto acids, hydroxy acids, α,β-unsaturated carbonyl compounds, and carbohydrates.

Suitable alcohols are believed to include methyl, ethyl, n-propyl, n-butyl, n-pentyl, n-hexyl, n-heptyl, n-octyl, n-decyl, lauryl, myristyl, cetyl, isopropyl, isobutyl, sec-butyl, tert-butyl, isopentyl, tert-pentyl, alkyl, crotyl, cyclopentanol, cyclohexanol, benzyl, α-phenylethyl, β-phenylethyl, and cinnamyl alcohol and the like. Preferred alcohols are those of the formula R—OH in which R represents an alkyl group with 1 to 6 carbon atoms.

Suitable ethers are believed to include methyl, ethyl, n-propyl, isopropyl, n-butyl, vinyl, alkyl, methyl tert-butyl, methyl-ethyl, diethyl, ethyl phenyl, phenyl, isopropyl phenyl, ether and anisole, 1,4-dioxane, tetrahydrofuran and the like.

Suitable carboxylic acids are believed to include formic, acetic, propionic, butyric, valeric, caproic, caprylic, capric, lauric, myristic, palmitic, stearic, oleic, linoleic, linolenic, phenylacetic, benzoic, toluic, chlorobenzoic, bromobenzoic, nitrobenzoic, phthalic, isophthalic, terephthalic, salicyclic, aminobenzoic, methoxybenzoic acid and the like.

Suitable aldehydes are believed to include formaldehyde, acetaldehyde, propionaldehyde, n-butyraldehyde, n-valeraldehyde, caproaldehyde, heptaldehyde, benzaldehyde, tolualdehyde, salicylaldehyde, p-hydroxybenzaldehyde, anisaldehyde, vanillin, piperonal and the like.

Suitable ketones are believed to include acetone, methyl ethyl ketone, 2-pentanone, 3-pentanone, 2-hexanone, 3-hexanone, methyl isobutyl ketone, acetophenone, propiophenone, n-butyrophenone, benzophenone and the like.

Suitable acid chlorides are believed to include acetyl, propionyl, n-butyryl, n-valeryl, stearoyl, benzoyl, p-nitrobenzoyl, 3,5-dinitrobenzoyl chloride and the like.

Suitable anhydrides are believed to include acetic anhydride and phthalic anhydride and the like.

Suitable amides are believed to include formamide, acetamide, propionamide, n-butyramide, n-valeramide, stearamide, benzamide and the like.

Suitable esters are believed to include methyl, ethyl, n-propyl, n-butyl, n-pentyl, isopentyl, benzyl and phenyl acetate, ethyl formate, ethyl propionate, ethyl n-butyrate, ethyl n-valerate, ethyl stearate, ethyl phenylacetate, ethyl benzoate and the like.

Suitable sulfonic acids are believed to include aromatic sulfonic acids such as benzenesulfonic, p-toluenesulfonic and m-nitrobenzenesulfonic acid and the like.

Suitable amines are believed to include aliphatic amines such as methylamine, dimethylamine, trimethylamine, ethylamine, diethylamine, triethylamine, n-Propylamine, di-n-propylamine, tri-n-propylamine, isopropylamine, nbutylamine, isobutylamine, sec-butylamine, tert-butylamine, cyclohexylamine, benzylamine, phenylethylamine, ethylenediamine, tetramethylenediamine, hexamethylenediamine, tetramethylammonium hydroxide and the like. Suitable amines also are believed to include aromatic amines such as aniline, methylaniline, dimethylaniline, diphenylamine, triphenylamine, toluidine, anisidine, chloroaniline, bromoaniline, nitroaniline, 2,4-dinitroaniline, 2,4,6-trinitroaniline, phenylenediamine, benzidine, p-aminobenzoic acid, sulfanilic acid, sulfanilamide, acetanilide, benzanilide, nitroacetanilide and the like.

Suitable phenols are believed to include phenol, cresol, fluorophenol, chlorophenol, bromophenol, iodophenol, aminophenol, nitrophenol, 2,4-dinitrophenol, 2,4,6-trinitrophenol, catechol, resorcinol, hydroquinone, alicyclic acid, eugenol, isoeugenol, anethole, vanillin, thymol, safrole and the like.

Suitable aryl halides ar believed to include fluorobenzene, chlorobenzene, bromobenzene, iodobenzene, fluorotoluene, chlorotoluene, bromotoluene, iodotoluene, difluorobenzene, dichlorobenzene, dibromobenzene, nitrochlorobenzene, 2,4-dinitrochlorobenzene, 2,4,6-trinitrochlorobenzene, vinyl chloride, vinyl bromide and the like.

Suitable glycols are believed to include ethylene glycol, propylene glycol, 1,3-propanediol, 1,2-butamediol, meso-2,3-butanediol, 1,4-butanediol, pinacol, glycerol, pentaerythritol, meso-hydrobenzoin, cis- and trans-1,2-cyclopentanediol, cis-and trans-1,2-cyclohexanediol and the like.

Suitable dicarboxylic acids are believed to include oxalic, malonic, succinic, glutaric, adipic, pimelic, suberic, azelaic, sebacic, maleic, fumaric, phthalic, isophthalic, terphthalic, hemimellitic, trimellitic, trimesic acid and the like.

Suitable keto acids are believed to include glyoxylic, pyruvic, acetoacetic, levulinic, o-benzoylbenzoic, β-benzoyl-propionic acid and the like.

Suitable hydroxy acids are believed to include glycolic, (+)-lactic, (±)-lactic, (±)-α-hydroxybutyric, (±)-mandelic, (−)-glyceric, (−)-malic, (±)-malic, (±)tartaric, (−)-tartaric, (±)-tartaric, mesotartaric, citric acid and the like; and β-propiolactone, γ-butyrolactone, γ-valerolactone, and the like.

Suitable, β-unsaturated carbonyl compounds are believed to include acrolein, crotonaldehyde, cinnamaldehyde, mesityl oxide, benzalacetone, dibenzalacetone, benzalacetophenone, dypnone, acrylic acid, crotonic acids, isocrotonic acid, methacrylic acid, sorbic acid, isocrotonic acid, methacrylic acid, sorbic acid, cinnamic acid, maleic acid, fumaric acid, maleic anhydride, methyl acrylate, methyl methacrylate, ethyl cinnamate, acrylonitrile, and the like.

Suitable carbohydrates are believed to include glucose, fructose, gluconic acid, glucaric acid, sorbitol, lucuronic acid, gulose, mannose, ribitol, xylose, xylaric acid, glucosides, pyranose, pyranosides, furanose, furanosides, (+)-maltose, (+)-cellobiose, (+)-lactose, (+)-sucrose, cellulose, amylose, amylopectin, and the like.

Applicants' invention has been found to be especially suitable for separating an alcohol, such as ethanol or isopropanol, from a mixture containing the alcohol and water. Mixtures of this type are obtained, for example, from a fermentation process or from the chemical production of alcohols, e.g., by reaction of water and propene. The dehydration of mixtures of an alcohol (an organic liquid) and water is especially of interest near the azeotropic composition where conventional separation by distillation becomes more difficult. Boiling points are closer together, energy consumption is higher, and eventually the processes have to be changed, e.g., from a simple distillation to an azeotropic distillation.

In a preferred aspect, this invention relates to a pervaporation process for separating, through thin, permselective membrane(s), an organic liquid from a feed mixture containing the organic liquid and water. The mixture is brought into contact with the upstream side of the membranes. A permeant, which is either a pure component of the feed mixture or a mixture enriched in one or more component(s) of the feed mixture is caused to permeate through the membranes as a gas phase by maintaining a low chemical potential for the permeate on the downstream side of the membranes. The permeate is withdrawn from the downside side of the membranes. The improvement in the process comprises using as the permselective membranes, sulfonated ion-exchange polyalkylene (polyalkene) membranes.

The low chemical potential for the permeant on the downstream side of the membranes is maintained by establishing a chemical potential gradient through the membranes so that one of the components in the membranes is preferably transported through the membranes. This chemical potential gradient may be established by, for example, differences, on opposed sides of the membranes, in the concentration of the components in the mixture, or, in the partial pressures. Differences in partial pressures may be established by applying at least a partial vacuum at the downstream side of the membranes. Differences in concentration of the components in the mixture on opposed sides of the membranes may be established by bringing the downstream side of the membranes in contact with a nonpermeable, acceptor fluid, preferably one which is compatible with only one of the components in the mixture, or, with a stream of hot gas.

The process according to this invention can be carried out in accordance with known techniques in the field of separation, using permselective sulfonated ion-exchange polyalkylene (polyalkene) membranes. For example, the pervaporation technique, in which non-porous semi-permeable membranes are used, is described in Hwang et al., *Membranes in Separations*, pp. 99–116, (John Wiley & Sons 1975), incorporated herein by reference.

Suitable linear polyalkylenes which may be sulfonated and have fixed ionic groups introduced thereinto have the formula: poly($C_2$-$C_{18}$ alkene). Examples of such polyalkenes include polyethylene, polypropylene, polybutylene, polyisobutylene, poly(1-butene), poly(3-methyl-1-butene), poly(1-pentene), poly(4-methyl-1-pentene), poly(1-hexene), poly(4-methyl-1-hexene), poly(5-methyl-1-hexene), poly(1-heptene), poly(5-methyl-1-heptene), poly(1-decene), poly(1-dodecene), poly(1-tetradecene), poly(1-hexadecene), poly(1-octadecene) and the like. Preferred is a linear polyethylene. For illustrative purposes, the description of the polyalkylene membrane used in the process of this invention will be made with reference to polyethylene.

The membranes used in the process of this invention are derivatives of chlorosulfonated polyalkylenes (polyalkenes), such as chlorosulfonated polyethylene, that were hydrolyzed after the sulfonation reaction to yield cationic exchange membranes, or, when quaternarized or treated with amine, provide anionic exchange membranes.

In general, processes for the chlorosulfonation of polyalkylenes, such as polyethylene, follow the principles of the so-called Reed process for the chlorosulfonation of hydrocarbons, described in U.S. Pat. No. 2,046,090 to Reed et al., the disclosure of which is incorporated herein by reference. The reaction is carried out in an anhydrous solvent (generally carbon tetrachloride) and the reacting agents are chlorine and sulfur dioxide. Sulfuryl chloride also may be used as an equivalent reagent. The reaction is a free-radical process and can be catalyzed by ultraviolet radiation or by radical sources, such as organic peroxides or azobisisobutyronitrile. The chlorosulfonation reaction is generally carried out at temperatures required to dissolve the polymer in the solvent. Superatmospheric pressures are often employed to achieve this result. The reaction is allowed to proceed until the chlorine content of the polymer is generally in the range of 20-45% and the sulfur content of the polymer is in the range of 1-2.5%.

After reaction, the polymer is isolated by any of several different techniques. If the polymer solution is steam distilled in the presence of surface-active materials, granular crumb-like particles can be obtained which may be dried by any conventional method. Alternatively, the polymer may be isolated as a reticulated film by evaporating the solvent from a thin film of solution on a smooth metal surface.

The preparation in the gas phase of chlorosulfonated polyethylene films is described in DeKörösy et al., British Pat. No. 98,562 and Jobst et al, 13 *Plaste Kautch* 579 (1966), incorporated herein by reference. In general, polyethylene is reacted with $SO_2$ and $Cl_2$ to produce sulfonyl pendant groups on the polyethylene which are subsequently hydrolyzed to the sulfonic version.

The preparation in the liquid phase of chlorsulfonated polyethylene films is described in Bikson, "Morphology and Properties of Heterogeneously Chlorosulfonated and Chlorinated Polyethylenes". PhD Thesis submitted to the Weizmann Institute of Science, Rehovot, Israel, October, 1980, incorporated herein by reference.

Polyethylene films, tubes, or hollow fibers may be chlorosulfonated by bringing them into contact with a carbon tetrachloride solution saturated with sulfur dioxide chlorine aseous mixture ($SO_2/Cl_2$ ratio of 2.5:1). See Vofsi et al., British Pat. No. 1,412,456. The reaction temperature is kept at 15° C. and methylethyl ketone hydroperoxide initiator is added continuously.

Solvent-swollen polyethylene powders also may be chlorosulfonated. Solvent-swollen powders of polyethylene are obtained by precipitation of vigorously stirred hot solutions (4% solution of low density polyethylene in $CCl_4$ at 70° C., and 4% solution of high density polyethylene in tetrachloroethane at 100° C.) with an excess of cold solvent. The precipitation is followed by chlorosulfonation of the solvent-swollen powders: $Cl_2$ and $SO_2$ gases are bubbled at high rates into the reaction mixture, cooled to 15° C., while a methylethyl ketone initiator and a cobalt naphthenate promotor are continuously added. The time interval that is necessary to bring the solution to 15° C. and to saturate it with $Cl_2$ and $SO_2$ gases in order to start the reaction, considerably affects the rate of the chlorosulfonation reaction. This is due to the fast deswelling of polyethylene powders at 15° C. and their partial crystallization. To suppress the latter effect, the reaction mixture may be brought to 15° C. by effective cooling and the reaction started in 1-2 minute time intervals.

After hydrolysis of the chlorosulfonated polyethylene film or quaternarization thereof with, e.g., a quarternary ammonium, phosphonium or an amine, the sulfonated ion-exchange polyethylene film may be equilibrated in an appropriate salt solution, e.g., 3M NaCl; CsCl, etc., washed with deionized water and placed in a pervaporation cell. The sulfonated ion-exchange polyethylene films which preferably may be used in this invention are commercially available. They have previously been used for electrodialysis.

An ion-exchange membrane consists of a matrix of hydrocarbon chains carrying fixed ionic groups. The area resistance of the membrane is usually less than 20 ohm-$cm^2$, in an univalent electrolyte. A membrane is termed a cation-exchange membrane if the fixed ionic group is acidic, and an anion-exchange membrane if the group is basic. Suitable fixed ionic groups for the cation-exchange membranes used in the process of this invention are a sulfonic group, a polyacrylic group, a carboxylic group a phosphorylic group and the like. Suitable counter ions for the cation-exchange membranes include $H^+$; alkali metals such as $Cs^+$, $Na^+$, $K^+$, $Li^+$, alkaline earth metals such as $Ba^{++}$, $Mg^{++}$, $Be^{++}$, $Ca^{++}$, $Sr^{++}$, $Ra^{++}$; $Al^{+++}$; transition metal ions such as $Fe^{++}$, $Fe^{+++}$, $Ni^{++}$, $Ni^{+++}$, $Cu^{++}$, $Cu^{+++}$ and the like. Also, organic cations comprised of quarternary amines or quaternary phosphonium may be used as counter-ions. Suitable fixed ionic groups for the anion-exchange membranes used in the process of this invention are quaternary ammonium, quaternary pyridinium, quaternary phosphonium, tertiary sulfonium, an amino or polyamino group, and the like. Suitable counter ions for the anion-exchange membranes include halides such as $Cl^-$, $F^-$, $Br^-$, $I^-$; oxides such as $NO_2^-$, $NO_3^-$, $PO_4^{-2}$; acids organic anions such as $CH_3COO^-$, $OH^-$; and the like.

High flux, high selectivity, and good physical and chemical stability are obtained by applicants' ion-exchange membrane. Such properties depend, in general, largely on the nature and composition of the fixed ionic groups and the matrix backbone; the balance of the hydrophilic and the hydrophobic content; degrees of cross linking and entanglement; porosity and asymmetry, if any; other physical and chemical posttreatments such as annealing, compression, and high-energy irradiation.

The sulfonated ion-exchange polyalkylene (polyalkene) films employed in the process of applicants' invention have a degree of sulfonation such that the charge density of the membrane is large enough to selectively permit one of the components in the feed mixture, e.g., water, to pass through the membrane, but not to the extent that it swells the membrane so much that both components in the mixture to be separated, e.g., both the alcohol and water, are passed through. The polymer matrix serves to hold together ion pair charges without letting the polymer dissolve.

The permselectivity of the membranes used in this invention can be selected by varying the amount of cationic groups or anionic groups attached to the sulfonated polyethylene films. Separation factors of about 1.1 to 80,000 can be achieved using the membranes in the process of this invention.

Also, the ionic groups can be changed from one cationic group to another or from a cationic group to an anionic group or vice versa to tailor the separation process to particular needs.

Sulfonated ion-exchange polyalkylene (e.g., polyethylene) membranes employed according to applicants' invention are at least about 20%, preferably between about 25% and 75%, and more preferably between about 30% and 60% amorphous in structure. The amorphous section of a polyalkylene, such as polyethylene, can be sulfonated. The crystalline (hard) section of polyethylene cannot be sulfonated. For sulfonated ion-exchange polyalkylene (e.g., polyethylene) membranes which are between 30% and 60% amorphous, a charge density between about 0.2 meq/gr and 4.5 meq/gr is preferred. Such charge density will be higher for more amorphous, sulfonated ion-exchange polyalkylene (e.g., polyethylene) membranes.

The membranes used according to the process of this invention will absorb between about 0.1% and 150% of their weight in water. This is, in large part, a measure of their degree of charge density. The ionic groups provide hydrophilic sites within the polymer which tend to swell and absorb water.

The membranes for use according to the invention can be prepared in a known manner from casting or spinning solutions by casting films or by spinning to give tubing or hollow fibers.

Thermoplastic polyalkylenes such as polyethylenes can be brought into the desired membrane form by the known methods of thermoplastic processing technology, such as extruding, calendering or injection molding, dry and wet spinning and casting.

These manufacturing processes are well known in the art.

In general, thinner membranes permit higher rates of permeation. However, since the sulfonated ion-exchange polyalkylene (polyalkene) membranes used in applicants' invention can have very high intrinsic permeability, it is not necessary to make the membranes as thin as possible. However, as is known, the membranes must have adequate strength and stability so that they can be handled and no fractures or weak points arise during use. Preferably, therefore, the thickness of the membranes according to the invention is between about 0.5 and 500 micrometers and preferably between about 10 and 100 micrometers.

Membranes of this type can be supported by any known supporting substrate in the appropriate structural forms, for the process according to the invention. Hollow fibers do not require a supporting substrate.

The membranes may be used in the form of films, tubes, tubing or hollow fibers in order to increase surface area and in order to achieve a maximum membrane surface area per unit volume, thus permitting the use of small apparatuses. Separation units of this type, which also are termed "modules", are known. Membranes made from hollow fibers and used in this invention have a diameter between about 50 and 1000 micrometers. Membranes made from tubes and used in this invention have a diameter between about 1000 micrometers and 4 cm.

The proces according to the invention can be carried out, as known in the art, both discontinuously and continuously and, likewise, in one stage or several stages, for example, in the form of a separation cascade with any desired number of separating stages. Also, the process according to the invention can be combined with a conventional distillation process for economies, e.g., by shifting from distillation to the process of this invention when the separation of the feed mixture has reach about 65%.

Specific embodiments illustrating the mode of preparation, formulation and application of sulfonated ion-exchange polyalkylene membranes in the separation process of this invention are set forth below.

EXAMPLE IA

Referring to FIG. 1, there is shown a schematic drawing of a pervaporation system employed in Example IA. There is shown a 400 ml stainless steel, high pressure cell 10 equipped with a magnetic stirrer 14, (actuated by stir place 15), which was employed to contain a feed liquid 12, consisting of an isopropanol water mixture or an ethanol-water mixture. The 400 ml cell 10 was placed in a vessel 16 containing a heated oil bath 18 to heat the feed mixture to a desired temperature. The feed mixture 12 was circulated on the upstream side 20 of, and over, a flat sheet sulfonated polyethylene membrane 22, while the downstream side 24 was evacuated to 0.1 to $25 \times 10^2$ Pa with a vacuum pump 26.

Permeate was removed from the downstream side 24 of the membrane 22 via line 28. The line 26 was provided with three-way valves 30, 32, 34 and 36 to regulate flow through line 28. When valve 30 (provided with vent 38) was in the fully open position, a McLeod vacuum gauge 38 on line 28 was able to be used to measure the vacuum pressure in line 28.

Also connected to line 28 were a series of vacuum trap condensers 40, 42, 44 cooled by liquid air which were used to collect the permeate. Operation of the system based on the schematic view shown in FIG. 1 is clear to those skilled in the art. For example, when valves 30 and 34 were in the closed position, permeate flowed in line 28 through open valve 32 and into collection traps 40 and/or 43 as desired and then through open valve 36 into collection trap 44.

Flat sheet ion-exchange sulfonated polyethylene membranes, 40.3 micrometers thick, displaying a charge density of 2.33 milequiv/g, were used. The membranes were prepared by gas phase sulfonation of polyethylene, with $SO_2 + Cl_2$, to yield sulfonyl chloride pendant groups that were subsequently hydrolyzed to the sulfonic version (the membranes were supplied by the Institute of Applied Research University of Ben Gurion in Beer Sheva, Israel). The membranes were equilibrated in an appropriate salt solution (e.g., 3M NaCl; CsCl and others) washed with de-ionized water and were placed in the pervaporation static cell as shown in FIG. 1. The permeation measurements were conducted in a pervaporation mode with a membrane surface area of 37.5 cm$^2$ and a downstream pressure of 0.1–1 Pa$\times 10^2$. The permeate were condensed in the liquid nitrogen traps 42, 43 and 44 and its composition was determined using a gas chromatograph and conductivity detector.

A separation factor, $\alpha$ was calculated as follows:

$$\alpha = (X_w/X_{alc})^P / (X_w/X_{alc})^F (w/alc)$$

wherein XW$^P$, Xalc$^P$, XW$^f$, Xalc$^f$ denote weight fractions of water and alcohol in the product and in the feed.

The separation of alcohol-water mixtures is especially of interest near the azeotropic composition where conventional separation by distillation becomes more difficult, energy consumption is higher, and eventually, the processes have to be changed, e.g., shifting from a simple distillation to azeotropic distillation. Results of the flat sheet membrane's separation (FIG. 1) near the azeotropic composition of isopropanol/water are shown in Table 1 below. Because most of the energy consumed in the separation of the ethanol/water mixture occurs at compositions of greater than about 85 wt. % ethanol, a feed mixture containing about 15 wt. % water was used to study the flat sheet membrane's separation capabilities in this instance, as are shown in Table 2.

TABLE 1

The effect of counter-ion on flux and separation of water-isopropanol mixture with sulfonated polyethylene membrane

| Counter Ion | Water In Feed wt. % | Water in Permeate wt. % | Separation $\alpha$(w/i-PrOH) | Flux g/m$^2$h |
|---|---|---|---|---|
| Cs$^+$ | 10.4 | >99.97 | >28709 | 200 |
| K$^+$ | 11.6 | 99.99 | 76199 | 96 |
| Na$^+$ | 11.4 | 99.99 | 77712 | 139 |
| Li$^+$ | 11.2 | 99.6 | 1974 | 181 |

TABLE 1-continued

The effect of counter-ion on flux and separation of water-isopropanol mixture with sulfonated polyethylene membrane

| Counter Ion | Water In Feed wt. % | Water in Permeate wt. % | Separation α(w/i-PrOH) | Flux g/m²h |
|---|---|---|---|---|
| H+ | 11.2 | 40.9 | 5.5 | 1041 |

TABLE 2

The effect of counter-ion on flux and separation of water-ethanol mixture with sulfonated polyethylene membrane (26° C.)

| Counter Ion | Water In Feed wt. % | Water in Permeate wt. % | Separation α(w/i-PrOH) | Flux g/m²h |
|---|---|---|---|---|
| Cs+ | 14.6 | 99.2 | 725 | 152 |
| K+ | 15.9 | 99.3 | 150 | 49 |
| Na+ | 15.6 | 99.2 | 671 | 80 |
| Li+ | 16.1 | 76.1 | 16.6 | 289 |
| H+ | 16.0 | 33.2 | 2.6 | 1364 |

The results shown in Tables 1 and 2 above show that one stage separation is attainable for these mixtures when a proper ion-exchange membrane was employed. The counter-ion's sequence, in regard to separation and flux, was reported. The cesium counter-ion surprisingly exhibited a much higher flux than the potssium and the sodium counter ions. The levels of separation achieved for this water alcohol mixture with applicants' process were never reported in the past. Intrinsic trans membrane fluxes were also very high if, indeed, the permation rate is proportional to the membrane thickness, as is the case in most instances where mass transport occurs through an isotropic membrane.

It is of interest to note that although the separation factors of the isopropanol-water mixture were much higher than that of the ethanol-water mixture, the permeation rate values were in the same order of magnitude. This is due to the fact that the permeate composition consists of almost pure water for all counter-ions, excluding H+ (and the Li+ versions in the water/ethanol mixture).

Figure 2:
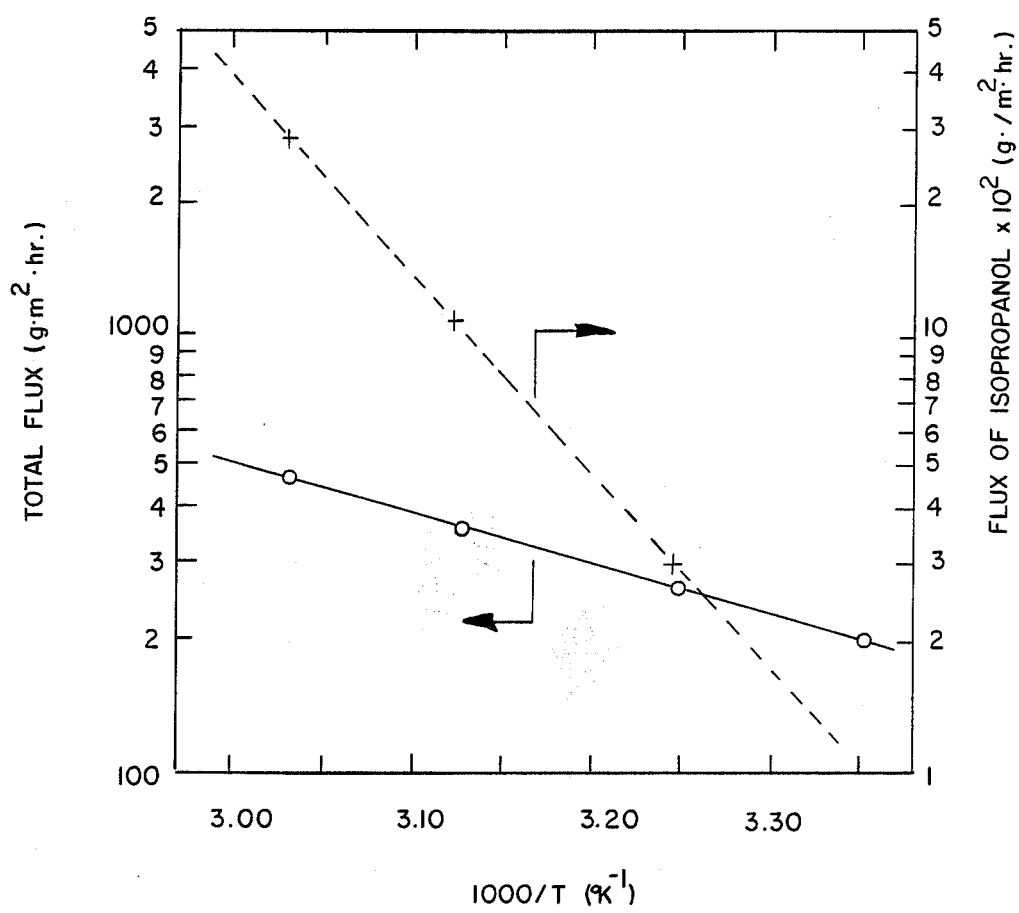
FIG. 2 is a semilog plot of total flux and isopropanol flux (g/m$^2$hr.) vs. reciprocal of absolute temperature (°K.$^{-1}$) for a separation of an isopropanol-water mixture according to the process of this invention.

Extremely low values for the apparent activation energy of transport (see Table 3 below) were recorded for this membrane (A charge density, Ea, of about 5 kcal/mole). These values are very close to the activation energy for the mobility of water in water, (about 4.5 Kcal/mole). It is believed that this result indicates that mass transport of the kind shown here, was that of transport through hydration shell and water clusters. The fact that the polyethylene sulfonated membrane contains 0.3-0.5 volume fraction of unpermeable crystalline dispersed phase, indeed supports the suggestion that the bulk of the permeation was conducted through the rather high charge-density segments of the membrane via continuous pathways from surface to surface; i.e., transport through extended micelle mechanism. The Ea of about 20 Kcal/mole calculated for the isopropanol fraction of the permeate (FIG. 2 herein) was an extremely high value that suggests that the isopropanol permeation occurred, at least in part, through the entire amorphous matrix of the membrane through conventional solution-diffusion mechanisms.

TABLE 3

The effect of feed temperature flux and separation factor of sulfonated polyethylene membrane, with Cs+ counter-ion.*

| No. | Feed Temperature (°C.) | Flux (g./m² · h) | Separation Factor (w/i-PrOH) |
|---|---|---|---|
| 1 | 25.5 | 200.0 | 28706 |
| 2 | 35.0 | 261.4 | 29329 |
| 3 | 47.0 | 352.0 | 29015 |
| 4 | 57.0 | 464.1 | 14502 |

*Feed composition: H₂O:Isopropanol - 11.6:88.4
Membrane thickness: 40.3 μm
Charge density - 2.33 milleq/g

EXAMPLE IB

Figure 3:
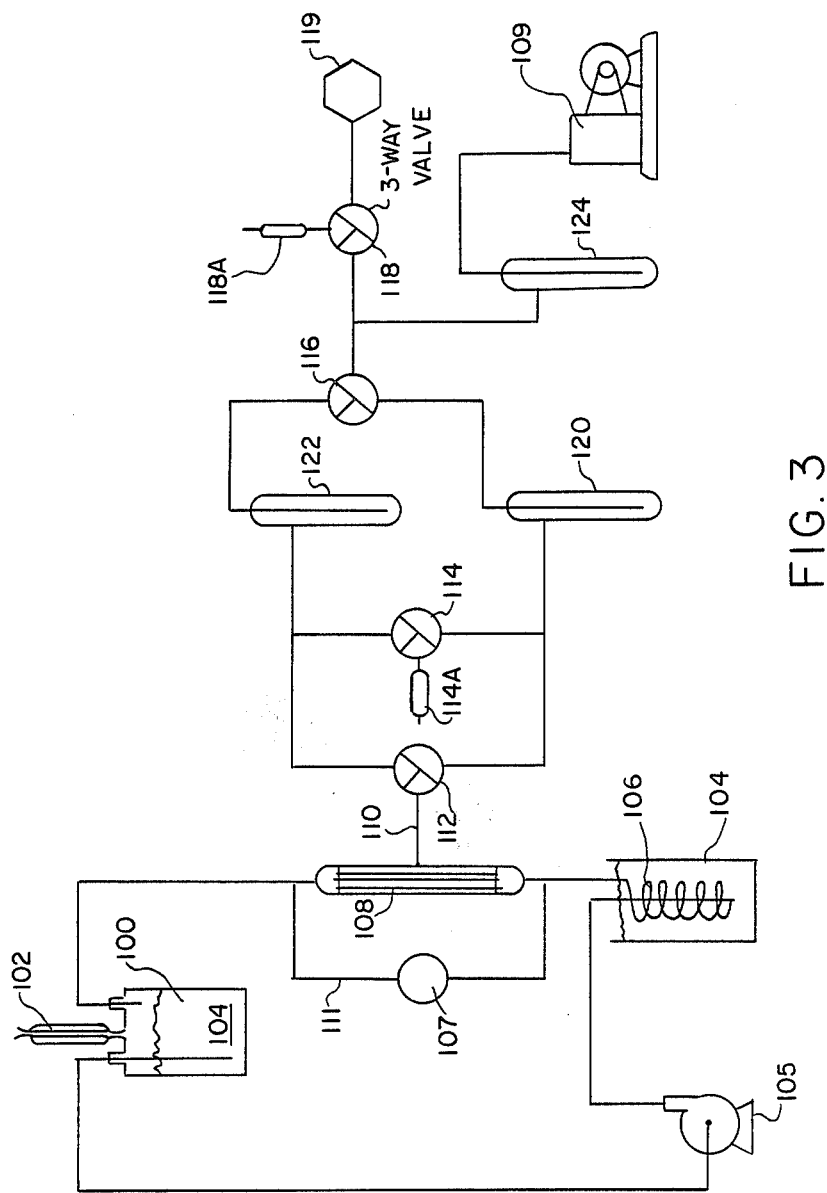
FIG. 3 is a schematic view of a pervaporation process employing a flow through cell of hollow fibers (or flat sheet membranes) according to this invention.

A pervaporation experiment was carried out using the pervaporation system described in Cabasso, 22 *I&EC Prod. Res. & Dev.* 313 (1983), incorporated herein by reference. This system is schematically shown in FIG. 3. There is shown a 400 ml container 100 which contains equipped with the feed liquid 104 a reflux condenser 102. Also shown is thermostated bath 106 and copper tubing coil, through which the feed liquid mixtures 104 flows through the thermostated bath. By pumping feed mixture from container 100 through the thermostated bath 106 which is directly connected to the membrane module 108, the temperature of the permeant was regulated. A digital differential thermocouple 107 on line 111 was used to monitor temperature of the feed mixtures 104 between the inlet and outlet of the hollow fiber membranes 108. This arrangement prevails also when a flat sheet membrane is used as 108 (mounted in a flow-through cell as described in Cabasso, 22 *I&EC Prod. Res & Dev.* 313 (1983)).

The feed mixture was circulated on the upstream side of the membranes 108 through the hollow fibers, while the downstream side was evacuated to 0.1 to 25×10² Pa with a vacuum pump 109. The hollow fibers or flat sheets used were made from sulfonated cation-exchange polyethylene and had a wall thickness of 0.01 mm. Their charge density was 2.1 meq/g, and the counter ions were the ones shown in Table 1. Flow rate through the hollow fiber unit was adjusted, so as to minimize concentration gradient along the fiber core due to the permeation of components through the wall. Flow rates were controlled by gear pump 105 having a Teflon head.

Permeate was removed from the downstream side of the hollow fiber membranes 108 via line 110. The line 110 was provided with three-way valves 112, 114, 116 and 118 to regulate flow through line 110 or segments thereof. Also connected to line 110 were a series of vacuum trap condensors 120, 122, 124 cooled by liquid air which were used to collect the permeate. Valve 118 was used to control access to a McLeod-Lippincott vacuum gauge 119 which was used to measure the vacuum pressure in line 110. Valves 118 and 114 have vents 118A and 114A to the atmosphere. Operation of the system based upon the schematic view shown in FIG. 3 is clear to those skilled in the art. For example, when valves 114 and 118 were in the closed position, permeate flowed in line 110 through open valves 112 and into collection traps 120 and/or 122, as desired, and then through open valve 116 into collection trap 124, if desired.

Figure 3A:
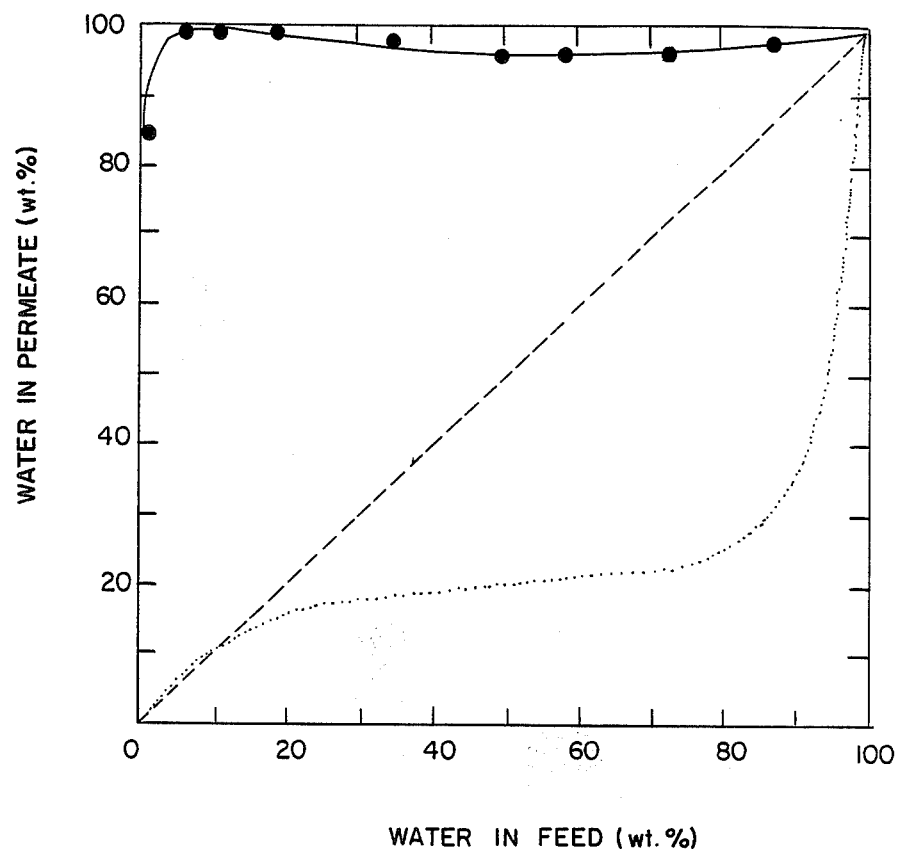
FIG. 3A is a plot of permeate composition vs. feed composition in the separation of an isopropanol-water with a sulfonated polyethylene membrane with Cesuim as a counter ion at 30° C., using the pervaporation technique shown in FIG. 3.

Using the above system shown in FIG. 3, similar results to those shown in Table 1 above were obtained using the hollow fiber membranes. The results are plotted in FIG. 3A.

EXAMPLE II

Examples IA and IB were repeated with different feed mixtures and membranes as follows:

Hollow fiber membrane experiments were run according to the process described in Example IB and flat sheet membrane experiments were run as described in Examples IA and IB.

Separation by pervaporation of water—methanol; ethanol; and isopropanol mixtures were investigated. The membranes used in this separation were the following:

(a) Sulfonated polyethylene anion-exchange membranes (1.2 meq/g) with a wall thickness of 0.10 mm and loaded with $Cl^-$ counter-ions.

(b) Sulfonated polyethylene cation-exchange membrane, (2.1 meq/g) with a wall thickness of 0.055 mm and loaded with $K^+$ counter-ions.

(c) Hollow fiber, sulfonated, cation-exchange polyethylene membrane having a wall thickness of 0.01 mm. The charge density was 2.1 meq/g. and the cationic group was the amino group.

Figure 4:
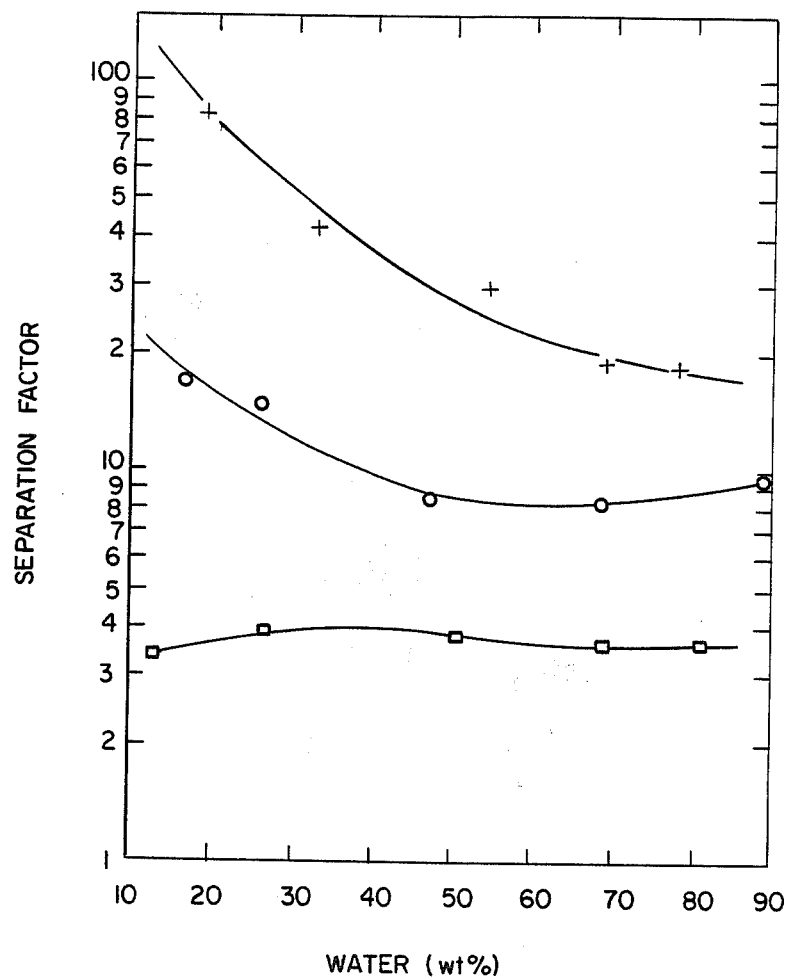
FIG. 4 is a semilog plot of separation factor vs. feed composition in separation of various alcohols from the aqueous solution by polyethylene anion exchange membranes.
Figure 5:
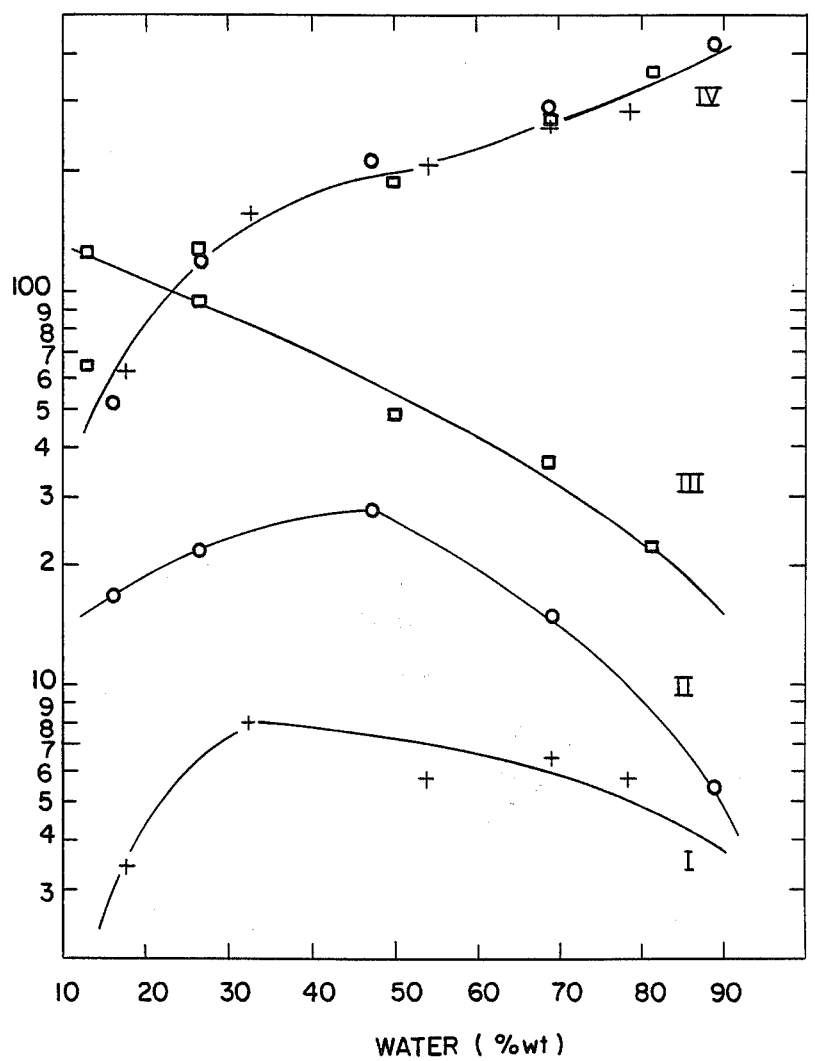
FIG. 5 is plot of the flux of alcohol vs. feed composition in the separation of water (wt. %).

Results are shown in Tables 4, 5 and 6 and FIGS. 4 and 5.

The permeation rate through the membrane decreased in the following order: water>methanol>ethanol>2-propanol. This generally followed the same order of molecular weight, polarity and the self diffusion coefficients, (i.e., 3.6, 2.5, 1.16, and $0.73 \times 10^{-5}$ cm$^2$/sec., respectively.) The separation factor between water and the alcohols increased in the reverse order: methanol<ethanol<isopropanol. (FIG. 4).

Figure 6:
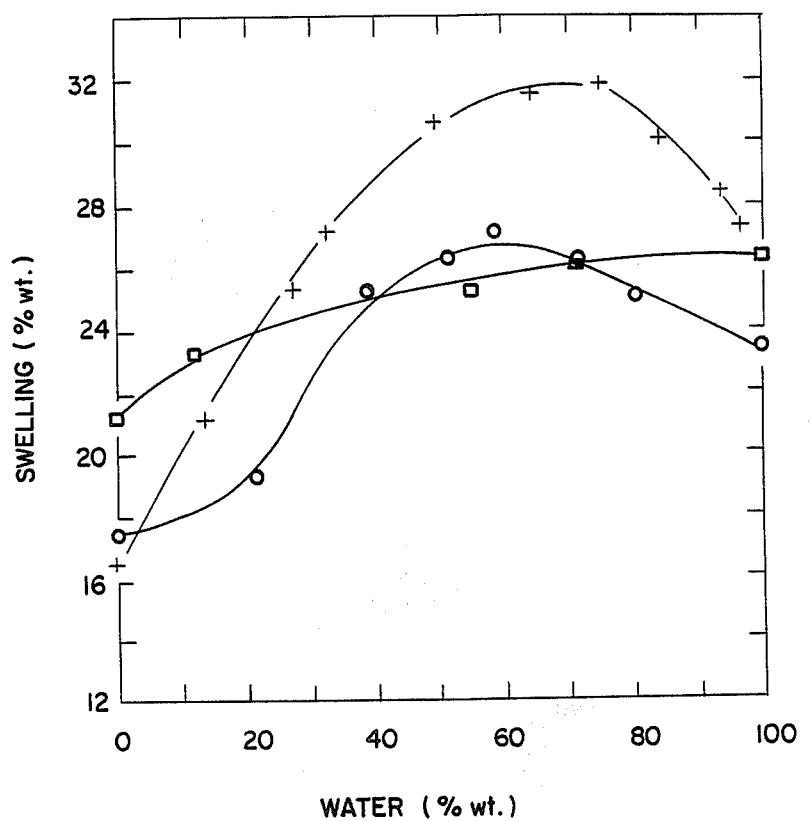
FIG. 6 is a plot of swelling (wt. %) of polyethylene anion exchange membrane vs. water concentration (wt. %) in the feed mixture of different alcohol water.

The flux of water and methanol increased with augmentation of methanol concentration in solution. Whereas the flux of ethanol was maximal at about 50 wt. % and flux of isopropanol was maximal at about 35 wt. % water; the flux of the latter, however, was marginal at very low concentrations of water in feed. (FIG. 5) The swelling curves of the anion exchange membrane in presence of alcohol-water mixtures (FIG. 6) show that there is a swelling maxima for the isopropanol and ethanol aqueous mixtures. The composition of the water-isopropanol in the membrane shows (Table 6) that water concentration in the membrane was proportional to the water molal fraction of the feed solution, whereas the isopropanol concentration in the membrane exhibited a plateau over a wide range of solution concentrations.

The hollow fibers used for separation of the three alcohols showed higher selectivity but lower flux than the anion exchange membrane. The thin cation exchange membrane (0.55 mm) was superior over the other membranes regarding flux and separation factor. It is noteworthy to mention that the permeability coefficient varies little when water concentration was above 20 wt. %.

As the concentration of isopropanol and water in the membrane did not change dramatically with the solution concentration, the permeability coefficient and separation factor were more or less constant over a wide zone of solution composition.

Figure 7:
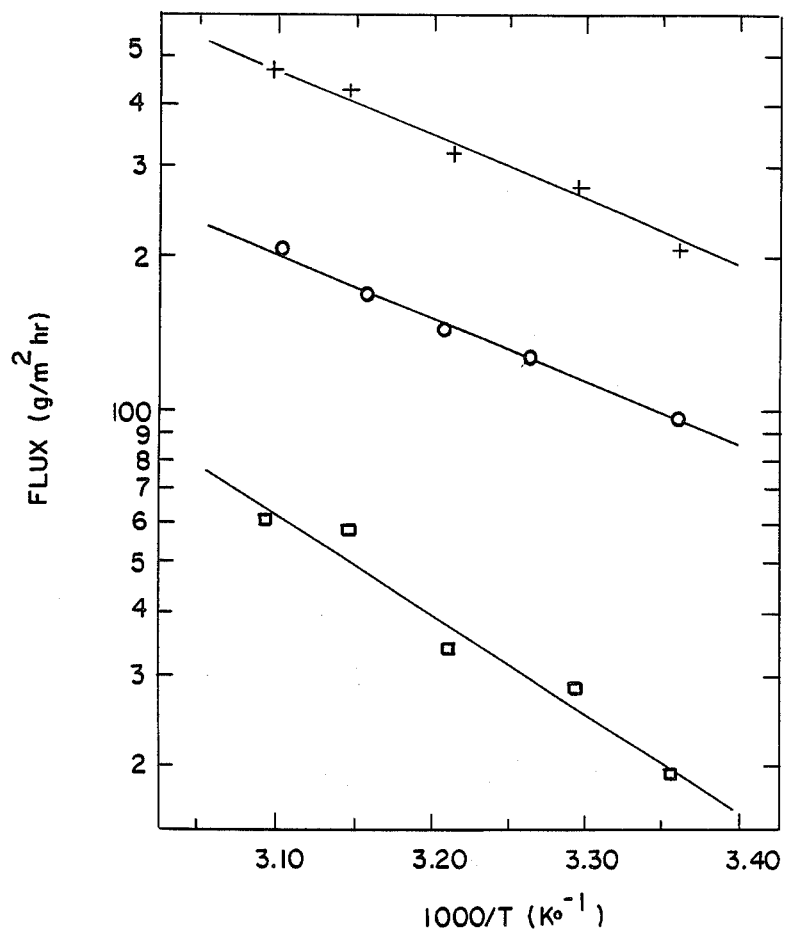
FIG. 7 is a semilog plot of water and ethanol flux (g/m$^2$hr.) vs. reciprocal of absolute temperature (°K.$^{-1}$) for the separation of an ethanol water mixture according to the process of this invention.

Semilog plots of water and ethanol flux versus reciprocals of absolute temperature (FIG. 7) show that the apparent energy of activation $E_{app}$ of water of 5.75 Kcal/mole and of ethanol 8.8 Kcal/mole.

These results indicate that the ion-exchange membranes can by employed in various forms, and are especially suited for the separation of aqueous solution of organic solutes.

TABLE 4

Separation of Pervaporation of Methanol-Water Mixtures with Polyethylene Ion-Exchange Membranes (24° C.)

| Feed Water wt. % | Flux Water wt. % | Flux Methanol wt. % | Product Water wt. % | Separation factor α |
|---|---|---|---|---|
| a. Anion-Exchange ($Cl^-$) 0.1 mm |||||
| 13.2 | 65.1 | 128.1 | 33.7 | 3.6 |
| 26.4 | 129.3 | 95.6 | 57.5 | 3.8 |
| 50.1 | 176.9 | 48.2 | 78.6 | 3.7 |
| 68.5 | 273.7 | 36.3 | 88.3 | 3.5 |
| 81.2 | 340.8 | 21.8 | 94.0 | 3.6 |
| b. Hollow Fibers Cation-Exchange ($Ca^{++}$) |||||
| 56.7 | 61.1 | 10.3 | 85.5 | 4.6 |
| 69.0 | 92.3 | 7.7 | 93.0 | 5.4 |

TABLE 5

Separation of Pervaporation of Water-Ethanol Mixtures with Polyethylene Ion-Exchange Membranes

| Feed H$_2$O (wt. %) | Flux Water | Flux Ethanol (g/m$^2$h) | Permeability $\bar{P} \times 10^8$ (cm$^2$/3° C.) | Product H$_2$O | Separation factor α | Temp. °C. |
|---|---|---|---|---|---|---|
| a. Anion-Exchange ($Cl^-$) 0.1 mm |||||||
| 16.1 | 52.9 | 17.1 | 7.5 | 75.6 | 16.1 | 24 |
| 16.6 | 117.6 | 22.0 | 10.5 | 84.3 | 15.0 | 24 |
| 47.7 | 212.9 | 28.1 | 10.9 | 88.7 | 8.6 | 24 |
| 69.5 | 285.0 | 15.0 | 10.8 | 95.0 | 8.3 | 24 |
| 88.9 | 428.0 | 5.4 | 13.1 | 98.7 | 9.9 | 24 |
| 22.6 | 125.9 | 24.1 | 13.0 | 83.9 | 17.8 | 32 |
| 22.6 | 147.7 | 41.6 | 16.6 | 78.5 | 12.5 | 38 |
| 22.6 | 169.4 | 43.1 | 17.4 | 79.7 | 13.4 | 43 |
| 22.6 | 203.6 | 54.8 | 21.0 | 78.8 | 12.8 | 49 |
| 47.0 | 271.2 | 28.8 | 14.1 | 90.4 | 10.6 | 31 |
| 47.0 | 316.8 | 33.2 | 16.5 | 90.5 | 10.6 | 37 |
| 47.0 | 440.8 | 59.2 | 23.0 | 88.2 | 8.4 | 45 |
| 47.0 | 464.6 | 60.4 | 24.2 | 88.5 | 8.7 | 50 |
| b. Hollow Fibers Cation-Exchange ($Ca^{++}$) |||||||
| 28.0 | 18.4 | 2.04 | 1.7 | 89.8 | 26.4 | 35 |
| 38.0 | 42.5 | 2.80 | 2.7 | 93.8 | 24.6 | 35 |
| 57.0 | 66.1 | 2.04 | 2.9 | 97.0 | 23.3 | 35 |
| 8.04 | 89.1 | 1.04 | 3.0 | 98.8 | 21.2 | 35 |
| c. Cation-Exchange ($K^+$) 0.55 mm |||||||
| 53.5 | 327.7 | 7.50 | 15.3 | 97.6 | 38.5 | 24 |

TABLE 6

Separation and Dehydration by Pervaporation of Water-Isopropanol Mixtures with Polyethylene Ion-Exchange Membranes

| Feed H$_2$O (wt. %) | Flux Water | Flux Ethanol (g/m$^2$h) | Permeability $\bar{P} \times 10^8$ (cm$^2$/s) | Product H$_2$O (wt. %) | Separation factor α | Temp. °C. |
|---|---|---|---|---|---|---|
| a. Anion-Exchange ($Cl^-$) 0.1 mm |||||||
| 17.9 | 63.2 | 3.5 | 8.1 | 94.8 | 81.4 | 24 |
| 32.5 | 158.7 | 8.0 | 11.6 | 95.4 | 41.3 | 24 |
| 54.4 | 207.0 | 5.5 | 9.5 | 97.4 | 31.3 | 24 |
| 69.3 | 260.2 | 6.4 | 9.7 | 97.6 | 18.0 | 24 |
| 78.3 | 287.0 | 4.7 | 9.8 | 98.5 | 17.1 | 24 |
| b. Hollow Fibers Cation-Exchange ($Ca^{+2}$) [OD = 1.1 mm, ID = 0.9 mm] |||||||
| 24.4 | 40.0 | 0.83 | 3.8 | 98.0 | 148.0 | 35 |
| 39.6 | 84.2 | 1.02 | 5.1 | 98.8 | 125.6 | 35 |
| 55.4 | 93.2 | 0.69 | 4.2 | 99.3 | 109.5 | 35 |
| 71.2 | 97.3 | 0.51 | 3.6 | 99.5 | 77.6 | 35 |
| 78.4 | 102.2 | 0.33 | 3.5 | 99.7 | 76.3 | 35 |
| c. Cation-Exchange ($K^+$) 0.55 mm |||||||
| 24.2 | 287.0 | 5.4 | 15.2 | 99.3 | 471.4 | 24 |

TABLE 6-continued

Separation and Dehydration by Pervaporation of Water-Isopropanol Mixtures with Polyethylene Ion-Exchange Membranes

| Feed $H_2O$ (wt. %) | Flux Water | Flux Ethanol (g/m²h) | Perm- eability $\bar{P} \times 10^8$ (cm²/s) | Product $H_2O$ (wt. %) | Separ- ation factor $\alpha$ | Temp. °C. |
|---|---|---|---|---|---|---|
| 66.8 | 474.2 | 9.5 | 18.4 | 98.1 | 25.7 | 24 |

EXAMPLE IIA

The flatsheet membrane anion-exchange sulfonated polyethylene membrane was submerged in different water-isopropanol solution compositions and then was equilibrated, and removed from the solution and checked for absorption of feed components into the membrane. The results are shown in Table 7. The membrane did not overswell; the maximum absorption was 32%.

TABLE 7

Liquid Composition in Polyethylene Anion-Exchange Membranes Equilibrated at Various Water-Isopropanol Concentrations

| Solution Composition Water Wt. % | Molal Fraction | Absorption Total[a] | Absorption Water[b] | Absorption Isopro- panol[b] | Absorption Ratio $H_2O$/i-PrOH |
|---|---|---|---|---|---|
| 0 | 0 | 16.4 | 0 | 2.70 | — |
| 14.3 | 0.36 | 21.6 | 6.5 | 1.75 | 3.72 |
| 23.5 | 0.50 | 24.5 | 9.8 | 1.65 | 5.94 |
| 27.5 | 0.56 | 25.4 | 11.0 | 1.60 | 6.88 |
| 38.8 | 0.68 | 28.5 | 12.2 | 1.60 | 7.63 |
| 52.9 | 0.79 | 31.0 | 12.4 | 1.53 | 8.10 |
| 75.0 | 0.91 | 32.0 | 14.4 | 1.10 | 13.09 |
| 100.0 | 1.00 | 26.5 | 14.6 | 0 | — |

[a]Absorbed liquid (g)/swollen membrane (g)
[b]Moles in one Kg of swollen membrane

EXAMPLE IIB

Figure 8:
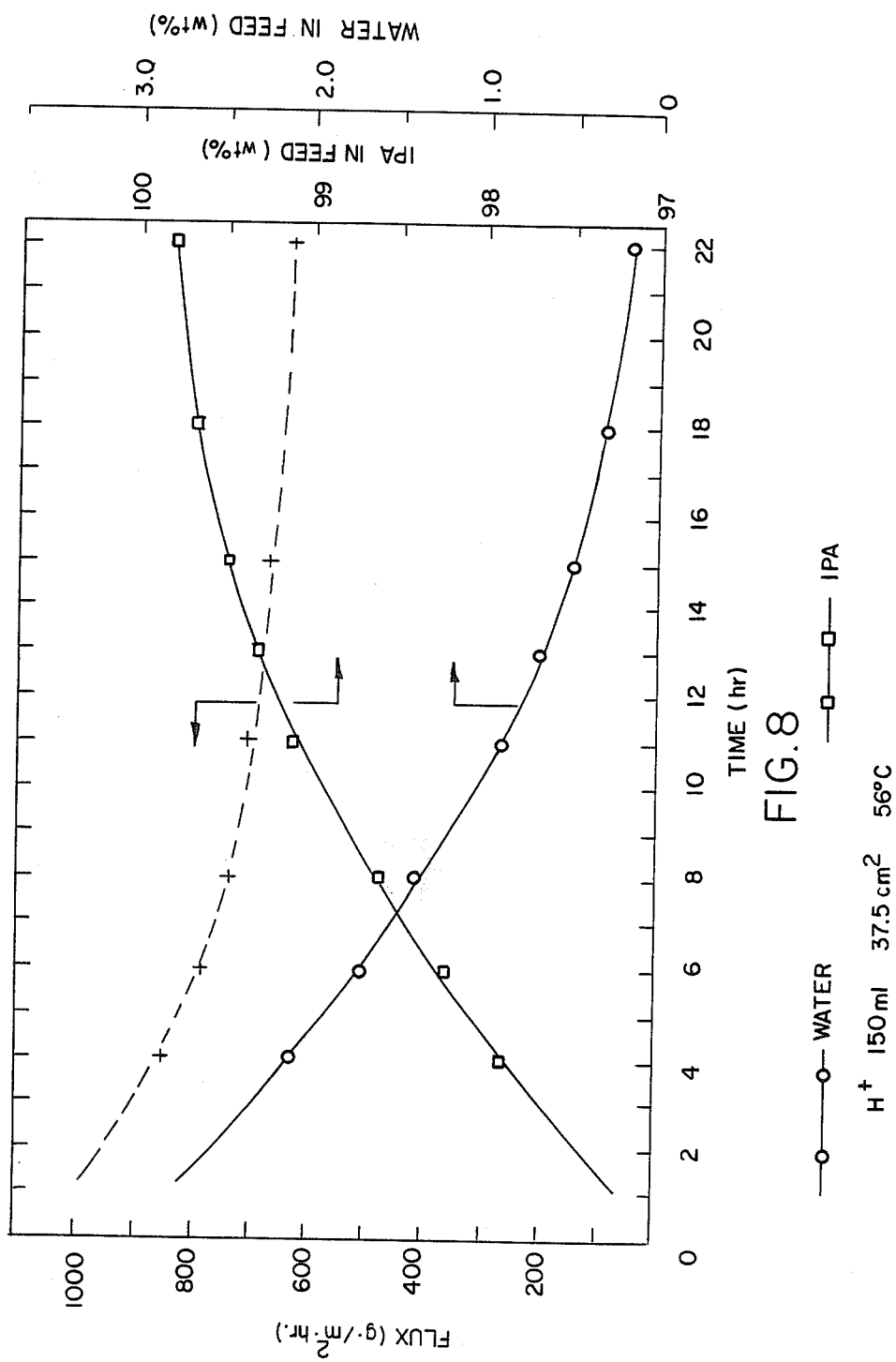
FIG. 8 is a plot of flux (g/m$^2$hr.) vs. time (hr.) and composition of isopropanol in the feed mixture (wt. %) in the dehydration of an isopropanol/water mixture according to the process of this invention.
Figure 9:
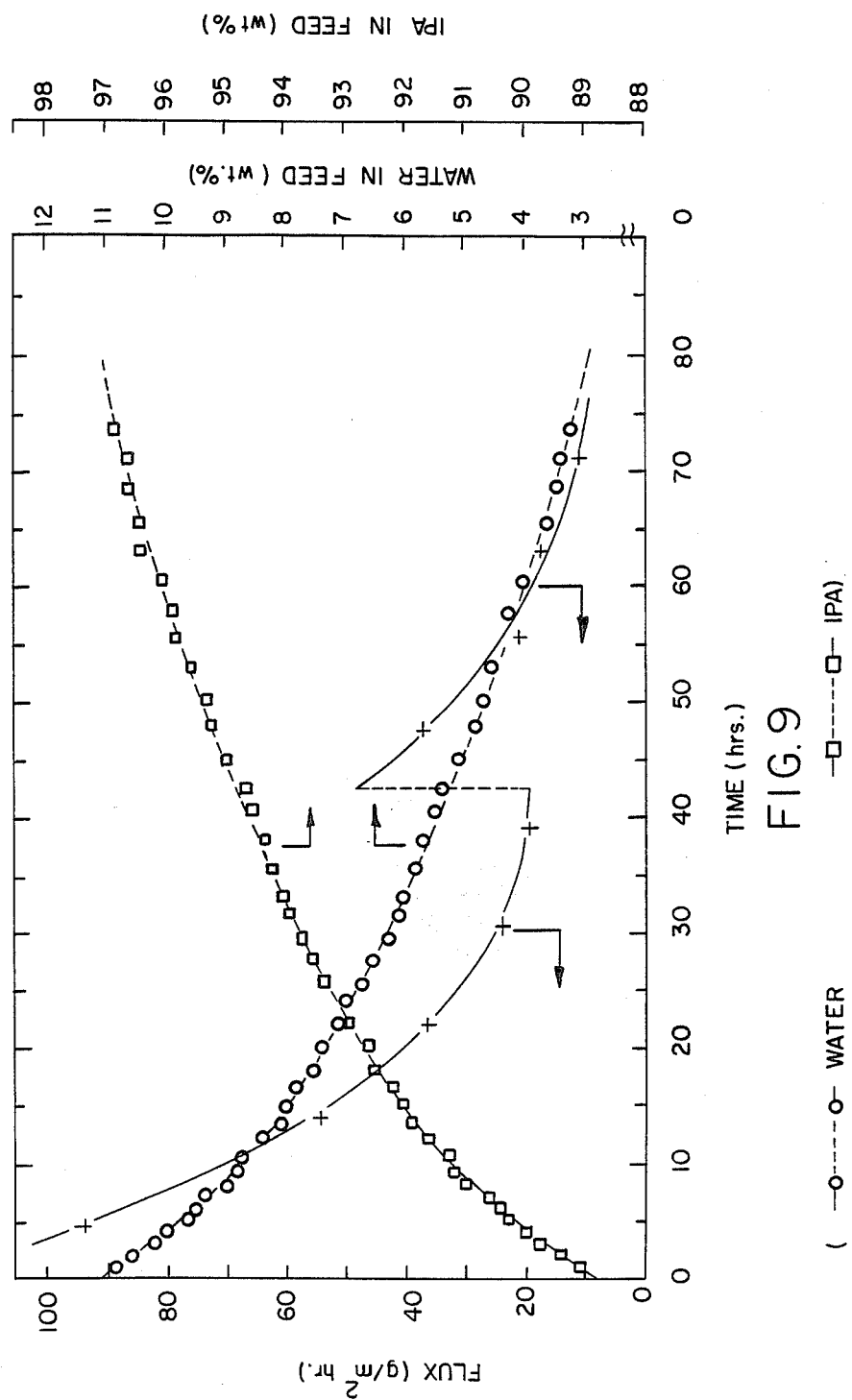
FIG. 9 is a plot of flux (g/m$^2$hr.) vs. time (hr.) and composition of isopropanol in the feed mixture (wt. %) in the continuous dehydration of an isopropanol/water mixture according to the process of this invention.

Concentration, by dehydration on of isopropanol-water azeotropic mixtures was conducted with hollow fiber membranes as described in Example II above (see FIGS. 8 and 9). As shown, the concentration of isopropanol in the feed was 99.9 wt. % when the experiment was stopped. An extremely high level of dehydration using membrane processes was recorded. Note that a sulfonated polyethylene ion-exchange membrane containing $C_s+$ counter-ion was used and that for the first 40 hrs, the temperature was 23° C. and then was increased to 56° C. to the end of the run (FIG. 9).

EXAMPLE III

Dehydration by Air Stripping

The permeation system of Example IB (FIG. 1) was used except that instead of vacuum, hot gas was used as the acceptor fluid.

Figure 10:
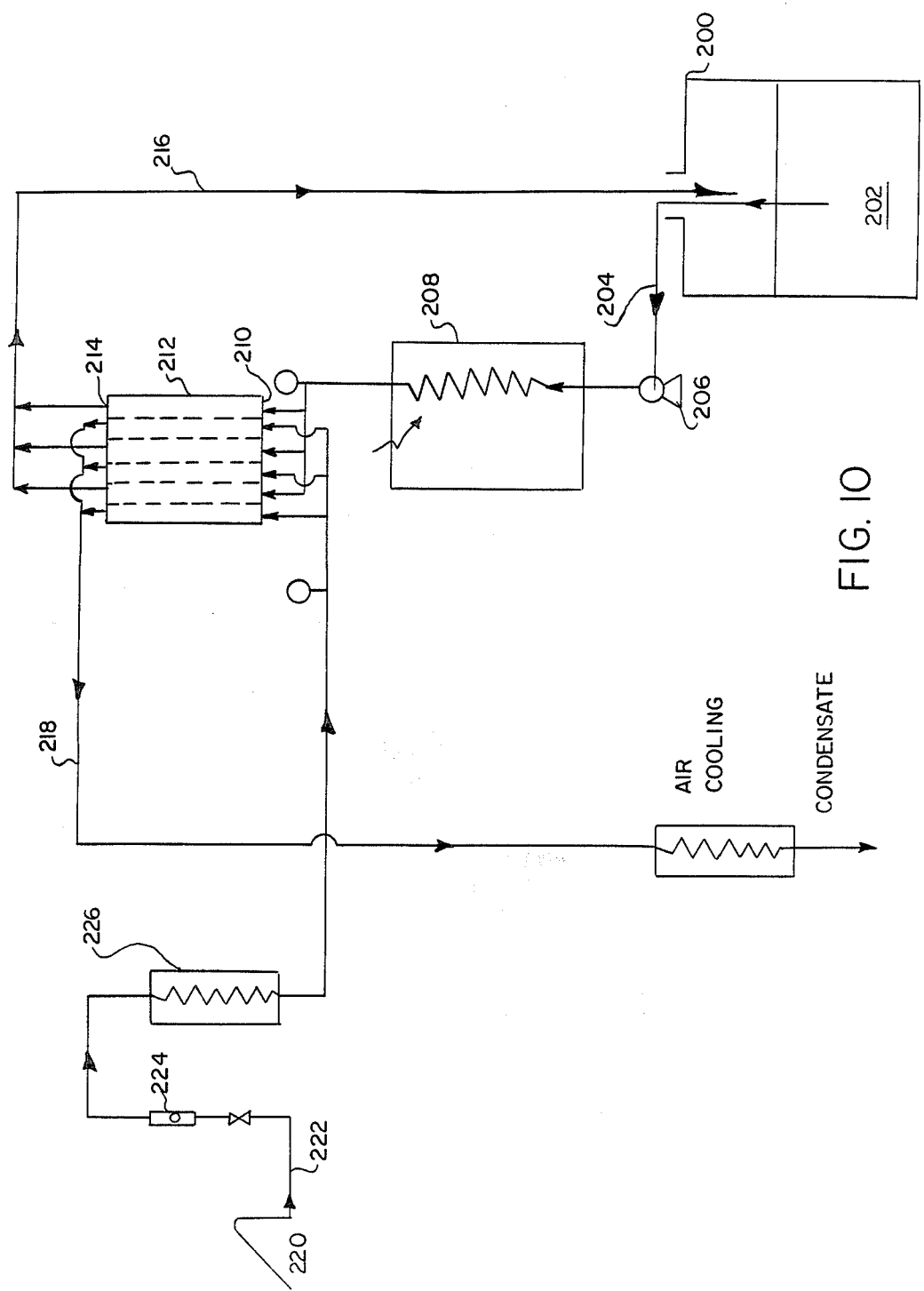
FIG. 10 is a schematic view of an embodiment of applicants' membrane separation process using air as an acceptor fluid.

Study of water-alcohol mixtures separation through ion-exchange membranes employing hot air as purge fluid was carried out in a bench scale, laboratory unit, with multi-compartments apparatus. The air was supplied at room temperature (24° C.) at 36% relative humidity (78 g/m³). The air passed through a hot (50°–70° C.) copper tube (⅜"). A schematic view of this system is shown in FIG. 10.

Shown in FIG. 3 is a feed reservoir 200 containing a feed mixture 202 (which can be obtained as outflow from a reactor). The feed mixture is pumped via line 204 by pump 206 into thermostated bath 208 (optional) where it may be heated to a desired temperature and fed into the upstream side 210 of the flat membrane cells 212. Permeant may be recycled to the feed reservoir 200 via line 216. Permeate is withdrawn from the upstream side 214 of the flat membrane cells and fed via line 218 for condensation via air cooling, or optionally, may be vented to the atmosphere. A source of pressurized air 220 is used to provide a lower chemical potential on the side of the flat membrane cells. The air is fed through line 222 and may be metered via flow meter 224 and optionally heated via preheater 226 to a desired temperature.

The outlet (copper coil) of the purge air was cooled down to 0° C. resulting in condensation of the permeate. The calculation of mass-transport through this system was conducted as follows:

The permeability constant (P) was calculated from the following equation:

$$J = \frac{P(C_1 - C_2)}{l}$$

Where:
J—flux, mole/sec. cm²
$C_1$—Upstream concentration mole/cm³
$C_2$—Downstream concentration mole/cm³
l—membrane thickness (cm)
P—permeability constant cm² sec$^{-1}$.

The ion exchange membranes of Example II were used in the air stripping process. Experimental results are shown in Tables 8 and 9 below. The results were excellent.

The pervaporation technique of the previous example (FIG. 10—hot air) was repeated using a flat cell membrane comprised of a stack of five membranes. The flat cell membrane has a surface area of 725 cm². An isopropanol-water mixture was dehydrated in one run.

A continuous process was run for 6 stages, calculations were done for each run and are reported in Table 8.

TABLE 8

Permeation through polyethylene cation exchange ($C_s^{++}$) membrane (0.055 mm) with hot air (52° C.) as acceptor fluid (membrane area 725 cm²)

| Stage | Feed Composition $H_2O$ wt. % | Air Humidity (max. %) | Flux (g/h · m²) $H_2O$ | Flux (g/h · m²) i-PrOH | Permeate $H_2O$ wt. % | Apparent Separation Factor | Permeability (P) cm²/s × 10⁷ |
|---|---|---|---|---|---|---|---|
| a. Isopropanol - $H_2O$ | | | | | | | |
| 1 | 9.9* | — | 1085.7 | 1.0 | 99.9 | 137.2 | — |
| 1 | 37.1–32.2 | 59 | 637.0 | 55.4 | 92.0 | 21.5 | 3.5 |
| 2 | 32.3–19.4 | 55 | 554.4 | 31.0 | 94.7 | 50.9 | 2.8 |
| 3 | 19.4–11.9 | 28 | 241.0 | — | 99.2 | 650.0 | 1.9 |

TABLE 8-continued

Permeation through polyethylene cation exchange ($C_s^{++}$) membrane (0.055 mm) with hot air (52° C.) as acceptor fluid (membrane area 725 cm²)

| Stage | Feed Composition H₂O wt. % | Air Humidity (max. %) | Flux (g/h · m²) H₂O | Flux (g/h · m²) i-PrOH | Permeate H₂O wt. % | Apparent Separation Factor | Permeability (P) cm²/s × 10⁷ |
|---|---|---|---|---|---|---|---|
| 4 | 11.9–9.1 | 23 | 82.6 | — | 98.4 | 524.0 | 0.97 |
| 5 | 9.1–7.0 | 18 | 32.3 | — | 98.6 | 810.0 | 0.5 |
| 6 | 7.0–6.7 | 18 | 12.4 | — | — | — | 0.23 |
| b. Ethanol - H₂O | | | | | | | |
| | 37.8–30 | 46 | 537.2 | 24.7 | 95.6 | 42.4 | 2.1 |
| | 30–19.8 | 36 | 336.4 | 7.9 | 97.7 | 127.4 | 1.7 |
| | 19.8–14.5 | 17 | 137.7 | — | 99.23 | — | 1.0 |

*This measurement was done on the small unit 35 cm² membrane's area

TABLE 9

Separation of ethanol-water mixture by air stripping method, employing polyethylene cation exchange ($C_s^{++}$) membranes

| Feed H₂O (wt. %) | Air Flow (24° C.) (wt. h) | Relative Humidity (%) Incoming (24° C.) | Relative Humidity (%) Heated (52° C.) | Relative Humidity (%) Exit (5° C.) | Product Composition H₂O (wt. %) | Apparent Separation Factor (w/e) |
|---|---|---|---|---|---|---|
| 89.4 | 240 | 36% | 22.0 | 100% | 99.87 | 66.4 |
| 80.8 | " | 36% | 21.1 | " | 99.81 | 89.2 |
| 62.3 | " | 36% | 19.1 | " | 99.54 | 89.0 |
| 49.9 | " | 36% | 15.2 | " | 99.54 | 110.0 |
| 37.8 | " | 36% | 12.9 | " | 99.52 | 163.7 |

ᵃMembrane area 35 cm², Feed temperature 52° C.

EXAMPLE IV

Dehydration by Osmotic Distillation

A. Example III was repeated except that instead of air as the circulatory fluid, the acceptor fluid (liquid) used was poly(ethyleneglycol) with a Mw of 200. This liquid was circulated facing the membrane's downstream side. Feed mixtures of alcohol-water mixtures were circulated in the upstream side. Different versions of polyethylene ion-exchange membranes were used (by replacing the counter-ions). The results are shown in Table 10 below. Water was the preferential permeate.

B. By changing the acceptor to a fluid that is not miscible with water, but miscible with alcohol (e.g., 1-octanol, 1-decanol, 1-dodecanol, 1-tetradeconal, and tributylphosphate were used each) the selectivity reversed; i.e., the alcohol permeated preferentially. Fluxes from 3 to 500 g/hr m² and separation factors of 20, 25, 30, 10, 11 were attained; respectively, using the five acceptor liquids mentioned above, with sulfonated polyethylene membranes in the Na-counter ion form.

TABLE 10

Water-Isopropanol separation by Osmotic distillation with sulfonate-polyethylene membranes. (60° C.) (Polyethylene glycol, 200 MW was used as acceptor fluid)

| Feed (H₂O %) | Flux of Water g/hr · m² | Flux of Isopropanol g/hr · m² | Separation factor, α | Temperature °C. |
|---|---|---|---|---|
| a. Cation exchange (Li⁺ form) Li⁺ - form (60° C.) | | | | |
| 100% | 1315 | — | — | |
| 72.2 | 1117.8 | 206.7 | 2.1 | |
| 66.5 | 662.8 | 140.6 | 2.5 | |
| 53.5 | 416.4 | 103.3 | 3.5 | |
| 26.2 | 221.0 | 190.9 | 3.3 | |
| 15.2 | 88.5 | 201.0 | 2.5 | |
| b. Cation exchange (K⁺ form) K⁺ - form (60° C.) | | | | |
| 100% | 889.2 | — | — | |
| 57.2 | 583.9 | 161.2 | 2.4 | |
| 46.2 | 429.6 | 98.8 | 5.7 | |
| 33.8 | 332.2 | 141.4 | 4.6 | |
| 26.4 | 289.3 | 292.3 | 2.9 | |
| 12.1 | 55.4 | 119.7 | 3.4 | |
| c. Cation exchange (Cs⁺ form) | | | | |
| 53.7 | 384.0 | 90.9 | 3.6 | |
| 38.9 | 297.5 | 45.3 | 10.3 | |
| d. Anion exchange (Cl⁻ form) | | | | |
| 26.9 | 1753.3 | — | — | 60 |
| 29.8 | 565.4 | 97.3 | 13.7 | 60 |
| 19.5 | 443.8 | 254.1 | 7.2 | 60 |
| 8.5 | 213.6 | 351.4 | 6.5 | 60 |
| 3.8 | 92.1 | 375.5 | 6.2 | 60 |
| 24.1 | 195.8 | 75.6 | 8.1 | 25 |
| e. Anion exchange (NO₃⁻ form) | | | | |
| 16 | 300.4 | 232.5 | 6.8 | 60 |
| 17.7 | 130.7 | 83.8 | 7.25 | 25 |
| f. Anion exchange (SO₄⁼ form) | | | | |
| 20.6 | 682.3 | 528.2 | 5.0 | 60 |
| 17.5 | 141 | 102.8 | 6.5 | 25 |
| g. Anion exchange (Br⁻ form) | | | | |
| 17.2 | 571.4 | 491.2 | 4.7 | 60 |
| 24 | 210 | 124 | 5.3 | 25 |
| h. Anion exchange (OH⁻ form) | | | | |
| 16 | 134.7 | 150.3 | 4.7 | 25 |

EXAMPLE V

HOLLOW FIBER-VACUUM TECHNIQUE

Dehydration of 1.4 Dioxan - water (85–15%) was carried on with the system shown in FIG. 3 by using hollow fiber sulfonated polyethylene membranes (with $Al^{+3}$ counter-ion) and 50 cm² surface area. The feed mixture was circulated at a temperature of 24.5° C. flux of 400 g/m²h and a separation of α=95 were obtained.

EXAMPLE VI

Dehydration of acetone-water (80:20) was conducted with sulfonated polyethylene hollow fiber membrane (with $Ba^{++}$ counterion). The experimental conditions were similar to that of Example V. Fluxes of 600 g/h.m² and a separation factor of 300 were obtained.

EXAMPLE VII

The system of FIG. 3 was used, except that the membrane had a charge density of 3.08 meq./g. Higher fluxes were obtained as shown in Table 12 below.

TABLE 12

The Effect Of Feed Composition On Flux And Separation Factor Of Sulfonated Polyethylene Membrane

| No. | Water content (wt. %) Feed | Water content (wt. %) Permeate | Separation factor (W/E) | Flux (g./m² · h.) Total | Flux (g./m² · h.) Water | Flux (g./m² · h.) Ethanol |
|---|---|---|---|---|---|---|
| 1 | 6.8 | 96.0 | 328.9 | 12.2 | 11.7 | 0.5 |
| 2 | 10.0 | 98.7 | 683.3 | 44.6 | 44.0 | 0.6 |
| 3 | 15.7 | 98.9 | 482.8 | 332.9 | 329.2 | 3.7 |
| 4 | 22.3 | 98.7 | 264.5 | 612.2 | 604.2 | 8.0 |
| 5 | 36.0 | 96.5 | 49.0 | 1428 | 1378 | 50 |
| 6 | 52.2 | 93.2 | 12.6 | 2699 | 2516 | 183 |
| 7 | 67.6 | 90.1 | 4.4 | 3842 | 3462 | 380 |
| 8 | 83.2 | 90.2 | 1.9 | 5159 | 4653 | 506 |
| 9 | 92.0 | 92.8 | 1.1 | 5734 | 5321 | 413 |
| 10 | 100 | 0 |  | 5803 |  |  |

Feed: Water - Ethanol
Feed Temperature: 26.5° C.
Membrane thickness: 53.2 (swollen in feed)
meq/g 3.08

EXAMPLE VIII

Using a pervaporation system as shown in FIG. 3, but with a flat sheet membrane flow cell, the effect of different amines as counter-ions was determined in two sulfonated polyethylenes with different charge densities. The membranes also were tested with a cesuim counter-ion as a reference. The results are set forth in table 11 below.

TABLE 11

The Effect of Different Amine Counter-Ions on Flux and Separation Factor of Sulfonated Polyethylene Flat Sheet Membranes.

| Flat Cell Membrane Charge Density (meq/g) | Counter-ion | Water Content (wt. %) Feed | Water Content (wt. %) Permeate | Flux g/m² · h | Separation Factor (w/i-PrOH) |
|---|---|---|---|---|---|
| 2.33 | $Cs^+$ | 12.5 | 99.95 | 166 | 14000 |
|  | $+[N(C_2H_5)_4]$ | 12.3 | 65.0 | 395 | 13.2 |
|  | $+[NH(C_2H_5)_4]$ | 11.3 | 59.6 | 405 | 10.4 |
|  | $+[(C_2H_5)_3N-CH_2CH_2]_2$ | 11.7 | 77.8 | 142 | 26.5 |
|  | $Cs^+$ | 12.3 | 99.94 | 220 | 11880 |
| 3.08 | $+[N(C_2H_5)_4]$ | 13.6 | 52.3 | 957 | 7.0 | feed: water (w) and isopropanol (i-PrOH)
feed temperature: 25.0° C.

EXAMPLE IX

A polyethylene flat sheet film was chlorsulfonated with chlorsulfonic acid in the liquid process described by Bikson previously herein. A membrane having a charge density of 1.2 meq./g and a thickness of 40 micrometers and using cesuim as a counter-ion was introduced into the pervaporation process shown in FIG. 1 and described previously herein. The feed temperature was 26.5° C. and the feed mixture consisted of water-ethanol (14.6 to 85.4 weight percent). Employing a vacuum of 1 mm Hg, the membrane produced a flux of 150 g/m²hr. with a separation factor of 415.

EXAMPLE X

Example IA was repeated using a Cesium counter-ion as shown in Table 1 and the pervaporation scheme shown in FIG. 1 and described previously herein. The membrane cell was pressurized with nitrogen to pressures of 100, 200, 500 and 800 psi. The separation factor measured decreased with the above increases in the pressures from 25,000 to 19,000 to 15,000 to 10,000, respectively, with no significant change in flux. The flux was about 200–250 g/m²hr. This shows that the membrane retained extremely high selectivity during high pressure operation.

What is claimed is:

1. In a process for dehydrating a feed mixture comprised of organic liquids using a polymer membrane having an upstream side and a downstream side wherein a permeant, which is a component of the feed mixture or a mixture comprised of the feed mixture enriched in one of its components, is caused to selectively sorb into the upstream side of the membrane and diffuse or flow through the membrane, and the permeant is desorbed on the downstream side of the membrane, the improvement which comprises:

using as said membrane a sulfonated ion-exchange polyalkene prepared by reacting, in the liquid or gas phase, chlorine and sulfur dioxide with a linear poly ($C_2$–$C_{18}$ alkene) in the presence of a free radical initiating catalyst or light to produce a chlorsulfonated polyalkene and subsequently either hydrolyzing the chlorsulfonated polyalkene to produce a cation-exchange sulfonated polyalkene or quaternarizing or treating the chlorsulfonated polyalkene with an amine to produce an anion-exchange sulfonated polyalkene, the sulfonated ion-exchange polyalkene having a degree of sulfonation which will permit said permeant to be selectively sorbed into said membrane, the ion-exchange polyalkene containing a counter-ion, said membrane being at least 20% amorphous in structure and having a charge density between about 0.2 meq/gr and about 4.5 meq/gr.

2. The process of claim 1 wherein the ion-exchange group of said membrane is an anion-exchange group selected from the group consisting of quaternary ammonium, quaternary phosphonium, tertiary sulfonium and an amino group, and the counter-ion is a negative charged ion selected from the group consisting of a halide, an oxide, an acid and OH.

3. The process of claim 1 wherein the ion-exchange group of said membrane is a cation exchange group selected from a sulfonic, a carboxylic, a phosphoric, a phosphinic, an arsonic and a selenonic group and the counter-ion is a positively charged ion selected from the group consisting of alkali metal ions, rare earth metal ions, transition metal ions, Al+++, and organic cations.

4. The process of claim 3 wherein the counter-ion is an alkali metal ion selected from the group consisting of Cs+, K+, Na+ and Li+.

5. The process of claim 1 wherein said membrane is between about 25% and about 75% amorphous in structure and has a charge density between about 2 meq/gr and about 4.5 meq/gr.

6. The process of claim 1 wherein said membrane is planar and has a thickness between about 0.1 micrometers and 500 micrometers.

7. The process of claim 6 wherein said membrane has a thickness between about 10 micrometers and about 100 micrometers.

8. The process of claim 1 wherein said membrane comprises a plurality of hollow fibers each having a diameter between 50 micrometers and about 1000 micrometers.

9. The process of claim 1 wherein said membrane comprises a plurality of tubes, each having a diameter between about 1000 micrometers and about 4 cm.

10. The process of claim 1 wherein a low chemical potential for the permeant which permeates through the membrane is provided at the downstream side of the membrane by circulating an acceptor fluid at the downstream side of the membrane and removing the phase which permeates through the membrane with said acceptor fluid and subsequently separating said phase from said acceptor fluid.

11. The process of claim 1 wherein a low chemical potential for the phase which permeates through the membrane is provided at the downstream side of the membrane by circulating a stream of gas at the downstream side of the membrane and removing the phase which permeates through the membrane with said gas stream and subsequently separating said phase from said gas stream.

12. The process of claim 1 wherein a low chemical potential for the phase which permeates through the membrane is provided at the downstream side of the membrane by circulating a stream of gas at the downstream side of the membrane and removing the phase which permeates through the membrane with said gas stream.

13. The process of claim 12 wherein the phase which permeates through the membrane is water and the gas is air.

14. The process of claim 13 wherein the permeate comprises at least about 95% by weight water.

15. The process of claim 1 wherein the organic compound in said mixture is selected from the group consisting of an alcohol, an ether, an aldehyde, a ketone, an acid chloride, an amide, an ester, a carboxylic acid, a dicarboxylic acid, a keto acid, a hydroxy acid, a carbohydrate, a sulfonic acid, an amide, an aryl halide, a phenol and a glycol.

16. The process of claim 15 wherein said organic compound is an alcohol.

17. The process of claim 16 wherein said alcohol has the formula: R—OH, wherein R represents an alkyl group having one to six carbon atoms.

18. The process of claim 17 wherein said alcohol is selected from the group consisting of isopropanol, methanol and ethanol.

19. The process of claim 15 wherein said organic compound is an ether.

20. The process of claim 19 wherein said ether is 1, 4-dioxane or tetrahydrofuran.

21. The process of claim 15 wherein said organic compound is a glycol.

22. The process of claim 15 wherein said organic compound is selected from the group consisting of an aldehyde, a ketone, an acid chloride, an aryl halide, an amide, a phenol, an ester and a carbohydrate.

23. The process of claim 15 wherein said organic compound is selected from the group consisting of a carboxylic acid, a dicarboxylic acid, a keto acid, a hydroxy acid and a sulfonic acid.

24. The process of claim 1 wherein the component of the first mixture which is selectively sorbed into and diffused through the membrane is water.

25. The process of claim 1 wherein the component of the first mixture which is selectively sorbed into and diffused through the membrane is said organic compound.

26. In a pervaporation process for dehydrating an organic liquid from a feed mixture containing the organic liquid in water using a thin-permselective membrane having an upstream side and a downstream side, wherein said mixture is brought into contact with the upstream side of the membrane, a permeant which is a component of the feed mixture of the feed mixture enriched in a component thereof is caused to permeate through the membrane as a gas phase by maintaining a low chemical potential for the permeant at the downstream side of the membrane, withdrawing the permeant from the downstream side of the membrane, and condensing and collecting the permeant as a liquid or solid, the improvement which comprises:
  employing as said membrane a sulfonated ion-exchange polyalkene prepared by reacting, in the liquid or gas phase, chlorine and sulfur dioxide with a linear poly ($C_2$–$C_{18}$ alkene) in the presence of a free radical initiating catalyst or light to produce a chlorsulfonated polyalkene and subsequently either hydrolyzing the chlorsulfonated polyalkene to produce a cation-exchange sulfonated polyalkene or quaternarizing or treating the chlorsulfonated polyalkene with an amine to produce an anion-exchange sulfonated polyalkene, the sulfonated ion-exchange polyalkene having a degree of sulfonation which will permit said permeant to be selectively sorbed into said membrane, said ion-exchange polyalkene containing a counter-ion, said membrane being between about 25% and about 75% amorphous in structure and having a charge density between about 0.2 meq/gr and about 4.5 meq/gr.

27. The process of claim 26 wherein said polyalkene is polyethylene.

28. The process of claim 27 wherein the ion-exchange group of said membrane is an anion exchange group selected from the group consisting of quaternary ammonium, a quaternary phosphonium, a tertiary sulfonium and polyamino groups, and the counter-ion is a negatively charged ion selected from the group consisting of a halide, an oxide, an acid and OH.

29. The process of claim 27 wherein the ion-exchange group of said membrane is a cation exchange group selected from a sulfonic, a carboxylic, a phosphoric, a phosphinic, an arsonic and a selenonic group, and the counter-ion is a positively charged ion selected from the group consisting of alkali metal ions, rare earth metal ions, transition metal ions, Al+++, and organic cations.

30. The process of claim 29 wherein the counter-ion is an alkali metal ion selected from the group consisting of Cs+, K+, Na+ and Li+.

* * * * *

UNITED STATES PATENT AND TRADEMARK OFFICE
CERTIFICATE OF CORRECTION

PATENT NO. : 4,728,429

DATED : March 1, 1986

INVENTOR(S) : Israel Cabasso, et al.

It is certified that error appears in the above-identified patent and that said Letters Patent is hereby corrected as shown below:

In Column 24, line 23, (Claim 26, line 7), change the second occurrence of "of" to --or--.

Signed and Sealed this

Twentieth Day of September, 1988

Attest:

DONALD J. QUIGG

*Attesting Officer*     *Commissioner of Patents and Trademarks*